(12) United States Patent
Bean et al.

(10) Patent No.: US 10,179,116 B2
(45) Date of Patent: *Jan. 15, 2019

(54) METHODS, COMPOSITIONS, AND KITS FOR TREATING PAIN AND PRURITIS

(71) Applicants: President and Fellows of Harvard College, Cambridge, MA (US); The General Hospital Corporation, Boston, MA (US)

(72) Inventors: Bruce P. Bean, Waban, MA (US); Clifford J. Woolf, Newton, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/470,324

(22) Filed: Mar. 27, 2017

(65) Prior Publication Data

US 2017/0319517 A1 Nov. 9, 2017

Related U.S. Application Data

(63) Continuation of application No. 14/496,629, filed on Sep. 25, 2014, now Pat. No. 9,603,817, which is a continuation of application No. 12/515,429, filed as application No. PCT/US2007/024174 on Nov. 19, 2007.

(60) Provisional application No. 60/997,510, filed on Oct. 3, 2007, provisional application No. 60/958,594, filed on Jul. 6, 2007, provisional application No. 60/860,124, filed on Nov. 20, 2006.

(51) Int. Cl.

| | | |
|---|---|---|
| *A61P 17/04* | (2006.01) | |
| *A61K 31/14* | (2006.01) | |
| *A61K 31/167* | (2006.01) | |
| *A61K 9/00* | (2006.01) | |
| *A61K 31/085* | (2006.01) | |
| *A61K 31/165* | (2006.01) | |
| *A61K 45/06* | (2006.01) | |

(52) U.S. Cl.
CPC .......... *A61K 31/167* (2013.01); *A61K 9/0014* (2013.01); *A61K 31/085* (2013.01); *A61K 31/14* (2013.01); *A61K 31/165* (2013.01); *A61K 45/06* (2013.01); *A61P 17/04* (2018.01)

(58) Field of Classification Search
CPC .... A61K 31/14; A61K 31/167; A61K 9/0014; A61P 17/04

See application file for complete search history.

(56) References Cited

U.S. PATENT DOCUMENTS

| | | |
|---|---|---|
| 3,519,631 A | 7/1970 | Jerchel et al. |
| 4,069,309 A | 1/1978 | Ciaudelli et al. |
| 5,591,317 A | 1/1997 | Pitts, Jr. |
| 5,747,470 A | 5/1998 | Becherer et al. |
| 5,783,683 A | 7/1998 | Morrison |
| 5,883,228 A | 3/1999 | Darnell, Jr. et al. |
| 6,355,637 B1 | 3/2002 | Axt et al. |
| 6,362,197 B1 | 3/2002 | Page et al. |
| 6,413,961 B1 | 7/2002 | Demopulos et al. |
| 6,825,190 B2 | 11/2004 | Moon et al. |
| 6,884,782 B2 | 4/2005 | Huang et al. |
| 7,705,004 B2 | 4/2010 | Song et al. |
| 8,138,339 B2 | 3/2012 | Bauer et al. |
| 8,143,412 B2 | 3/2012 | Priebe et al. |
| 8,258,144 B2 | 9/2012 | Song et al. |
| 9,603,817 B2 | 3/2017 | Bean et al. |
| 2003/0105126 A1 | 6/2003 | Demopulos et al. |
| 2003/0166629 A1 | 9/2003 | Choi et al. |
| 2004/0146590 A1 | 7/2004 | Iadarola et al. |
| 2004/0220187 A1 | 11/2004 | Stephenson et al. |

(Continued)

FOREIGN PATENT DOCUMENTS

| | | |
|---|---|---|
| CA | 2717042 A1 | 9/2009 |
| CN | 101156851 A | 4/2008 |

(Continued)

OTHER PUBLICATIONS

Rathmell et al. "Assessment of differential sensory blockade using QX-314 and capsaicin in large animals," Presentation No. PW 233. 12th World Congress on Pain Itinerary Planner, Glasgow, Scotland: International Association for the Study of Pain, Abstract Only, <www.abstractsonline.com>, retrieved on Jan. 31, 2008, (2 pages).
Jasmin et al., "The Cold Plate as a Test of Nociceptive Behaviors: Description and Application to the Study of Chronic Neuropathic and Inflammatory Pain Models," Pain 75:367-382 (1998).
Partial European Search Report for European Patent Application No. EP 11007949.8-2112, dated Jun. 22, 2012 (19 pages).
Owsianik et al., "Permeation and selectivity of TRP channels," Annu Rev Physiol. 68:685-717 (2006).

(Continued)

*Primary Examiner* — Theodore R. West
(74) *Attorney, Agent, or Firm* — Clark & Elbing LLP

(57) ABSTRACT

The invention features a method for inhibiting one or more voltage-gated ion channels in a cell by contacting the cell with (i) a first compound that activates a channel-forming receptor that is present on nociceptors and/or pruriceptors; and (ii) a second compound that inhibits one or more voltage-gated ion channels when applied to the internal face of the channels but does not substantially inhibit said channels when applied to the external face of the channels, wherein the second compound is capable of entering nociceptors or pruriceptors through the channel-forming receptor when the receptor is activated. The invention also features a quarternary amine derivative or other permanently or transiently charged derivative of a compound that inhibits one or more voltage-gated ion channels when applied to the internal face of the channels but does not substantially inhibit said channels when applied to the external face of the channels.

8 Claims, 9 Drawing Sheets

(56) References Cited

U.S. PATENT DOCUMENTS

| | | |
|---|---|---|
| 2005/0009016 A1 | 1/2005 | Moskowitz et al. |
| 2005/0090557 A1 | 4/2005 | Muhammad et al. |
| 2005/0142596 A1 | 6/2005 | Krolewski et al. |
| 2005/0152957 A1 | 7/2005 | Cleary et al. |
| 2005/0277680 A1 | 12/2005 | Priebe et al. |
| 2006/0062739 A1 | 3/2006 | Hofmann et al. |
| 2006/0100272 A1 | 5/2006 | Maniar |
| 2006/0106020 A1 | 5/2006 | Rodgers et al. |
| 2006/0183906 A1 | 8/2006 | Rodgers et al. |
| 2007/0135461 A1 | 6/2007 | Rodgers et al. |
| 2007/0149469 A1 | 6/2007 | Korherr |
| 2007/0149506 A1 | 6/2007 | Arvanitis et al. |
| 2008/0188500 A1 | 8/2008 | Arvanitis et al. |
| 2008/0312212 A1 | 12/2008 | Collingwood et al. |
| 2009/0054485 A1 | 2/2009 | Gleich et al. |
| 2009/0060898 A1 | 3/2009 | Kandimalla et al. |
| 2009/0162333 A1 | 6/2009 | Pays et al. |
| 2010/0098685 A1 | 4/2010 | Zhu et al. |
| 2010/0113416 A1 | 5/2010 | Friedman et al. |
| 2010/0120781 A1 | 5/2010 | Neamati |
| 2012/0022142 A1 | 1/2012 | Jadhav et al. |
| 2012/0129867 A1 | 5/2012 | Bauer et al. |
| 2012/0195902 A1 | 8/2012 | Friedman et al. |

FOREIGN PATENT DOCUMENTS

| | | |
|---|---|---|
| CN | 101347427 A | 1/2009 |
| DE | 100 39 449 A1 | 7/2003 |
| JP | 2006-522832 A | 10/2006 |
| JP | 2009-520700 A | 5/2009 |
| JP | 6205133 B2 | 9/2017 |
| WO | WO-98/24428 A1 | 6/1998 |
| WO | WO-98/37896 A1 | 9/1998 |
| WO | WO-99/11252 A2 | 3/1999 |
| WO | WO-99/63985 A1 | 12/1999 |
| WO | WO-01/44192 A1 | 6/2001 |
| WO | WO-01/44218 A1 | 6/2001 |
| WO | WO-01/45678 A2 | 6/2001 |
| WO | WO-2004/012757 A2 | 2/2004 |
| WO | WO-2004/110423 A1 | 12/2004 |
| WO | WO-2005/089206 A2 | 9/2005 |
| WO | WO-2005/117981 A1 | 12/2005 |
| WO | WO-2006/10587 A1 | 2/2006 |
| WO | WO-2006/010587 A1 | 2/2006 |
| WO | WO-2006/065722 A2 | 6/2006 |
| WO | WO-2007/071055 A1 | 6/2007 |
| WO | WO-2008/063603 A2 | 5/2008 |
| WO | WO-2009/114139 A2 | 9/2009 |
| WO | WO-2010/017996 A1 | 2/2010 |
| WO | WO-2011/133474 A2 | 10/2011 |
| WO | WO-2012/030912 A1 | 3/2012 |
| WO | WO-2012/162394 A2 | 11/2012 |

OTHER PUBLICATIONS

Taylor et al., "Persistent cardiovascular and behavioral nociceptive responses to subcutaneous formalin require peripheral nerve input," J Neurosci. 15(11):7575-7584 (1995).
Lim et al., "The Quaternary Lidocaine Derivative, QX-314, Produces Long-lasting Local Anesthesia in Animal Models In Vivo," Anesthesiology 107:305-311 (2007).
Yeh, "Sodium inactivation mechanism modulates QX-314 block of sodium channels in squid axons," Biophys J. 24(2):569-74 (1978).
Office Action for Canadian Patent Application No. 2,668,652, dated May 6, 2016 (4 pages).
Kawamata et al., "Effects of systemic administration of lidocaine and QX-314 on hyperexcitability of spinal dorsal horn neurons after incision in the rat," Pain. 122(1-2):68-80 (2006).
Kirkpatrick et al., "Comparison of the effects of procaine, chlorpromazine and their quaternary derivatives on nerve action potentials," Res Commun Chem Pathol Pharmacol. 1(1):149-155 (1970).
Wood et al., "Voltage-gated sodium channel blockers; target validation and therapeutic potential," Current Topics in Medicinal Chemistry, 5(6):529-537 (2005). Abstract Only.
Office Action for South Korean Application No. 10-2009-7012908, dated May 14, 2013 (7 pages).
Kochegarov, "Pharmacological modulators of voltage-gated calcium channels and their therapeutical application." Cell Calcium. 33(3):145-62 (2003).
Mizogami et al., "Local anesthetics adsorbed onto infusion balloon," Anesth Analg. 99(3):764-8 (2004).
Bonjardim et al., "Nociceptive behavior induced by mustard oil injection into the temporomandibular joint is blocked by a peripheral non-opioid analgesic and a central opioid analgesic," Pharmacol Biochem Behav. 91:321-326 (2009).
Cahalan et al., "Interactions between quaternary lidocaine, the sodium channel gates, and tetrodotoxin," Biophys J. 27(1):39-55 (1979).
Bley, "Recent developments in transient receptor potential vanilloid receptor 1 agonist-based therapies," Expert Opin Investig Drugs. 13(11):1445-56 (2004).
Rich et al., "Quaternary quinidine derivatives as a tool to study: block of human potassium channels," Biophys J. 66(2):A143 (1994).
Leffler et al., "The Vanilloid Receptor TRPV1 is Activated and Sensitized by Local Anesthetics in Rodent Sensory Neurons," J. Clin. Invest. 118:763-776 (2008).
Clare et al., "Voltage-gated sodium channels as therapeutic targets," Drug Discovery Today. 5(11):506-520 (2000).
Cao, "Voltage-gated calcium channels and pain," Pain. 126(1-3):5-9 (2006).
Schwarz et al., "Effects of QX-314 on membrane properties of neurons in the ventrobasal thalamus," Proc West Pharmacol Soc. 45:29-31 (2002).
McClesky, "A Local Route to Pain Relief," Nature 449:545-546 (2007).
Eller et al., "High affinity interaction of mibefradil with voltage-gated calcium and sodium channels.," Br J Pharmacol. 130(3):669-77 (2000).
Curtis et al., "The Mechanism of Action of Local Anesthesia by Tetraethylammonium Derivatives," Anesthesiology 54:270-277 (1981).
Schwarz et al., "Lumbar intrathecal administration of the quaternary lidocaine derivative, QX-314, produces neurotoxicity in mice," Can. J. Anaesth. 55(1):473931 (Abstract Only) (2008).
Meyers et al., "Lighting up the Senses: FM1-43 Loading of Sensory Cells through Nonselective Ion Channels," J. Neurosci. 23:4054-4065 (2003).
Examination Report for EP Application No. 07862114.1-2112 dated Sep. 23, 2009 (11 pages).
Woolf et al., "Neuropathic pain: aetiology, symptoms, mechanisms, and management," Lancet. 353(9168):1959-64 (1999).
Strichartz, "The inhibition of sodium currents in myelinated nerve by quaternary derivatives of lidocaine," J Gen Physiol. 62(1):37-57 (1973).
Nielsen et al., "Assessment of the combined approach of N-alkylation and salt formation to enhance aqueous solubility of tertiary amines using bupivacaine as a model drug," Eur J of Pharm Sci. 24(1):85-93 (2005).
Gerner et al., "Spinal Tonicaine: Potency and Differential Blockade of Sensory and Motor Functions," Anesthesiology 92:1350-1360 (2000).
Extended European Search Report pertaining to European Patent Application No. 11007950.6-2112, dated Feb. 27, 2012 (14 pages).
Stys et al., "Tertiary and quaternary local anesthetics protect CNS white matter from anoxic injury at concentrations that do not block excitability.," J Neurophysiol. 67(1):236-40 (1992).
Notice of Reasons for Rejection for Japanese Patent Application No. 2014-015120, dated Aug. 25, 2015 (5 pages).
Hahn et al., "Neuromyotonia in hereditary motor neuropathy," J Neurol Neurosurg Psychiatry. 54:230-5 (1991).
Gribkoff, "The role of voltage-gated calcium channels in pain and nociception." Semin Cell Dev Biol. 17(5):555-64 (2006).
Sullivan et al., "Synergistic inhibition of lysophosphatidic acid signaling by charged and uncharged local anesthetics," Anesth Analg. 88(5):1117-24 (1999).
Igakuno ayumi, Vik. 167, No. 2, 1993, pp. 118-121.

(56) References Cited

OTHER PUBLICATIONS

Hahnenkamp et al., "Local anaesthetics inhibit signalling of human NMDA receptors recombinantly expressed in Xenopus laevis oocytes: role of protein kinase C," Br J Anaesth. 96(1):77-87 (2006).
Tanelian et al., "Sodium channel-blocking agents: Their use in neuropathic pain conditions," Pain Forum. 4(2):75-80 (1995).
Office Action for Chinese Patent Application No. 201410034926.2, dated May 24, 2016 (8 pages).
International Search Report for International Application No. PCT/US2009/001541 dated Nov. 2, 2009.
Woolf, "Evidence for a central component of post-injury pain hypersensitivity," Nature. 306(5944):686-8 (1983).
Binshtok et al. "Lidocaine targets entry of the impermeant sodium channel blocker QX-314 into nociceptors to produce long-lasting regional analgesia," Program No. 170.6./KK27 2008 Neuroscience Meeting Planner. Washington, D.C.: Society for Neuroscience, 2008 (1 page). Online.
Omana-Zapata et al., "QX-314 inhibits ectopic nerve activity associated with neuropathic pain," Brain Res. 771:228-237 (1997).
Ikoma et al., "The neurobiology of itch," Nat Rev Neurosci. 7(7):535-47 (2006).
Japanese Patent Office Communication dated Sep. 18, 2012, in Japanese Patent Application No. 2009-537235 (6 pages).
EPO Communication for European Application No. 07862114.1, dated Sep. 23, 2009 (11 pages).
Kalso et al., "Sodium channel blockers in neuropathic pain," Current Pharmaceutical Design. 11(23):3005-11 (2005). Abstract Only.
Triggle, "The pharmacology of ion channels: with particular reference to voltage-gated Ca2+ channels," Eur J Pharmacol. 375(1-3):311-25 (1999).
Binshtok et al., "Inhibition of nociceptors by TRPV1-mediated entry of impermeant sodium channel blockers," Nature 449:607-610 (2007).
Donner et al., "New generation anticonvulsants for the treatment of epilepsy in children." NeuroRx. 3(2):170-80 (2006).
Kutchai et al., "Inhibition of the Na, K-ATPase of canine renal medulla by several local anesthetics," Pharmacol Res. 43(4):399-403 (2001).
Wang et al., "N-butyl tetracaine as a neurolytic agent for ultralong sciatic nerve block.," Anesthesiology. 85(6):1386-94 (1996).
Canadian Office Action for Canadian Patent Application No. 2,668,652, dated Jul. 22, 2014 (3 pages).
Frazier et al., "The site of action and active form of local anesthetics. II. Experiments with quaternary compounds," J. Pharmacol. Exp. Ther. 171:45-51 (1970).
McGivern et al., "Voltage-Gated Calcium Channels as Targets for the Treatment of Chronic Pain," Curr. Drug Targets CNS Neurol. Disord. 3:457-478 (2004).
Wang et al., "Quaternary ammonium derivative of lidocaine as a long-acting local anesthetic," Anesthesiology. 83(6):1293-1301 (1995) (6 pages).
Written Opinion of the International Searching Authority for International Application No. PCT/US2007/024174 dated Oct. 6, 2008.
Hellwig et al., "TRPV1 Acts as Proton Channel to Induce Acidification in Nociceptive Neurons," The Journal of Biological Chemistry 279:34553-34561 (2004).
Nielsen et al., "Bioreversible quaternary n-acyloxymethyl derivatives of the tertiary amines bupivacaine and lidocaine-synthesis, aqueous solubility and stability in buffer, human plasma and simulated intestinal fluid." Eur J Pharm Sci. 24:433-40 (2005).
Winkelman et al., "Inhibition of the A-type K+ channels of dorsal root ganglion neurons by the long-duration anesthetic butamben," J Pharmacol Exp Ther. 314(3):1177-86 (2005).
Grantham et al., "Fluspirilene block of n-type calcium current in NGF-differentiated PC12 cells." Br J Pharmacol. 111:483-8 (1994).
International Preliminary Report on Patentability for International Application No. PCT/US2007/024174 dated Jun. 4, 2009.
Office Action for Chinese Patent Application No. 201410034926.2, dated Jul. 23, 2015 (13 pages).

European Patent Office Communication pertaining to Application No. 07862114.1-2112, dated Sep. 15, 2011 (10 pages).
Jia et al., "TRPV1 receptor: a target for the treatment of pain, cough, airway disease and urinary incontinence," Drug News Perspect. 18(3):165-71 (2005). Abstract only.
Chen et al., "Differential Blockade of Nerve Injury-induced Thermal and Tactile Hypersensitivity by Systemically Administered Brain-penetrating and Peripherally Restricted Local Anesthetics," J. Pain 5:281-289 (2004).
Allen et al., "Clinical relevance of the neurotrophins and their receptors," Clin Sci (Lond). 110(2):175-91 (2006).
European Patent Office Communication pertaining to European Patent Application No. 11007949.8-2112, dated Feb. 17, 2012 (11 pages).
Puopolo et al. "Permeation and Block of TRPV1 channels by cationic local anesthetics," Program No. 628.11/C51. 2008 Neuroscience Meeting Planner. Washington, DC: Society for Neuroscience, 2008 (2 pages). Online.
Gribkoff, "Voltage-gated sodium channels in spinal ganglia: Tempting targets for new pain medications," Drug Discov Today. 3(4):585-91 (2006).
Amir et al., "The role of sodium channels in chronic inflammatory and neuropathic pain," J Pain. 7(5 Suppl 3):S1-29 (2006).
International Search Report for International Application No. PCT/US2007/024174 dated Oct. 6, 2008.
Bautista et al., "Fire in the hole: pore dilation of the capsaicin receptor TRPV1," Nat Neurosci. 11(5):528-9 (2008).
Yanagidate et al., "Local anesthetics," Handb Exp Pharmacol. 177:95-127 (2006).
Translation of Office Acton for Chinese Patent Application No. 200780050131.9, dated Feb. 23, 2011.
Gerner et al., "Capsaicin Combined with Local Anesthetics Preferentially Prolongs Sensory/Nociceptive Block in Rat Sciatic Nerve," Anesthesiology 109:872-878 (2008).
Qu et al., "Molecular determinants of drug access to the receptor site for antiarrhythmic drugs in the cardiac Na+ channel.," Proc Natl Acad Sci USA. 92(25):11839-43 (1995).
Yaksh, "Calcium channels as therapeutic targets in neuropathic pain," J Pain. 7(1 Suppl 1):S13-30 (2006).
Birklein et al., "Neuropeptides, neurogenic inflammation and complex regional pain syndrome (CRPS)," Neurosci Lett. 437:199-202 (2008).
Hunter et al. "The Contribution of Peripheral Sensory Neuronal Input towards the Maintenance of Neuropathic Pain" Soc Neurosci. 21:1411 (1995). (Abstract Only).
Bley et al., "Extracellular application of QX-314 blocks sodium channels and causes local anesthesia," Soc Neurosci. 21:1820 (Abstract 716.7) (1995).
Dux et al., "Inhibition of the neurogenic inflammatory response by lidocaine in rat skin," Inflamm Res. 45(1):10-3 (1996).
Blumberg, "Lighting a backfire to quench the blaze: A combined drug approach targeting the vanilloid receptor TRPV1," Molecular Interventions 7:310-312 (2007).
Bochner et al. "Immunological aspects of allergic asthma," Annu. Rev. Immunol. 12:295-335 (1994).
Szallasi et al., "The vanilloid receptor TRPV1: 10 years from channel cloning to antagonist proof-of-concept," Nat Rev Drug Discov. 6(5):357-72 (2007) (17 pages).
Ni et al., "Thermal sensitivity of isolated vagal pulmonary sensory neurons: role of transient receptor potential vanilloid receptors," Am J Physiol Regul Integ Comp Physiol. 291(3):R541-50 (2006).
Office Action for Canadian Patent Application No. 2,767,646, dated Nov. 1, 2017 (3 pages).
Vieira et al. "Effect of ricinoleic acid in acute and subchronic experimental models of inflammation," Med of Inflam. 9(5):223-228 (2000).
Holmdahl G, et al. A substance P antagonist, [D-Pro2, D-Trp7,9]SP, inhibits inflammatory responses in the rabbit eye Science. Nov. 27, 1981;214(4524):1029-31.
Lundberg JM, et al. Vascular permeability changes and smooth muscle contraction in relation to capsaicin-sensitive substance P afferents in the guinea-pig. Acta Physiol Scand. Feb. 1984;120(2):217-27.

(56) References Cited

OTHER PUBLICATIONS

Examination Report for Australian Patent Application No. 2016262678, issued Oct. 13, 2017 (4 pages).
Caceres et al., "A sensory neuronal ion channel essential for airway inflammation and hyperreactivity in asthma," Proc Natl Acad Sci U S A. 106(22):9099-104 (2009).
W.M. Edmondstone, "Chest pain and non-respiratory symptoms in acute asthma," Postgrad Med J 76(897):413-414 (2000).
Office Action for European Application No. 10797919.7, dated Jul. 19, 2013 (12 pages).
Office Action for Japanese Application No. 2012-519763, dated Jun. 23, 2015 (4 pages).
NCBI Blast for Accession No. CAQ09089.1. Retrieved on Jun. 9, 2015 (2 pages).
Office Action for Chinese Patent Application No. 200980117485.X, dated Nov. 23, 2011 (10 pages).
Perez-Reyes, "Molecular physiology of low-voltage-activated T-type calcium channels," Physiol Rev. 83(1):117-61 (2003).
Genovese et al., "Association of trypanolytic ApoL1 variants with kidney disease in African Americans," Science. 329(5993):841-5 (2010).
Office Action in U.S. Appl. No. 13/404,725 dated Aug. 26, 2013 (11 pages).
NCBI Blast for Accession No. NP_003652.2. Retrieved on Jun. 9, 2015 (3 pages).
NCBI Blast for Accession No. AF305224.1. Retrieved on Jun. 9, 2015 (2 pages).
"Bcl-2-regulated apoptosis: mechanism and therapeutic potential," available in PMC Sep. 29, 2009, published in final edited form as: Curr Opin Immunol. 19(5):488-96 (2007) (14 pages).
Juengst, "What next for human gene therapy? Gene transfer often has multiple and unpredictable effects on cells," BMJ 326(7404):1410-1 (2003).
Wan et al., "Apolipoprotein L1, a novel Bcl-2 homology domain 3-only lipid-binding protein, induces autophagic cell death," J Biol Chem. 283(31): 21540-9 (2008).
Molina-Portela et al., "Distinct roles of apolipoprotein components within the trypanosome lytic factor complex revealed in a novel transgenic mouse model," J Exp Med. 205(8):1721-8 (2008).
Duchateau et al., "Apolipoprotein L, a new human high density lipoprotein apolipoprotein expressed by the pancreas. Identification, cloning, characterization, and plasma distribution of apolipoprotein L," J Biol Chem. 272(41):25576-82 (1997).
Extended European Search Report for European Patent Application No. 15002768.8, dated Nov. 24, 2015 (9 pages).
NCBI Reference SNP(refSNP) Cluster Report: rs73885319, <http://www.ncbi.nlm.nih.gov/projects/SNP/snp_ref.cgi?rs=73885319>, retrieved Dec. 15, 2011 (3 pages).
Tzur et al. "Missense mutations in the APOL1 gene are highly associated with end stage kidney disease risk previously attributed to the MYH9 gene," Hum Genet. 128(3):345-50 (2010).
Summons to Attend Oral Proceedings pursuant to Rule 115(1) EPC for European Patent Application No. 10797919.7, dated Apr. 17, 2015 (7 pages).
Office Action for Chinese Patent Application No. 200980117485.X, dated Apr. 23, 2013 (11 pages).
English translation of Office Action for Chinese Patent Application No. 201080040830.7, dated Mar. 8, 2013 (14 pages).
Carr, "Neuroimmunology: Adding insult to allergy," Nat Rev Neurosci. 16(8):444 (2015).
Talbot et al., "Silencing Nociceptor Neurons Reduces Allergic Airway Inflammation," Neuron. 87(2):341-54 (2015).
Office Action for Chinese Patent Application No. 200980117485.X, dated Feb. 24, 2014 (9 pages).
Hunt et al., "Treatment of asthma with nebulized lidocaine: a randomized, placebo-controlled study," J Allergy Clin Immunol. 113(5):853-9 (2004).
Gibson et al., "The human serum resistance associated gene is ubiquitous and conserved in Trypanosoma brucei rhodesiense throughout East Africa," Infect Genet Evol. 1(3):207-14 (2002).

"Target neurons to relieve asthma," Nature. 523:8-9 (2015).
Office Action for Chinese Patent Application No. 200980117485.X, dated Oct. 24, 2012 (24 pages).
Written Opinion for International Application No. PCT/US2009/001541, dated Nov. 2, 2009 (8 pages).
Ferrarelli,"Allergic sensations fuel asthma," Sci Signal. 8(387):ec201 (2015).
NCBI Blast for Accession No. BC127186.1. Retrieved on Jun. 9, 2015 (3 pages).
Written Opinion of the International Searching Authority for International Application No. PCT/US2011/32924, dated Apr. 9, 2012 (8 pages).
International Preliminary Report on Patentability for International Application No. PCT/US2007/024174, dated May 26, 2009 (20 pages).
Van Hamme et al., "The trypanosome lytic factor of human serum and the molecular basis of sleeping sickness," Int J Parasitol 34(8):887-98 (2004).
Gentry et al., "Local Anesthetics Noncompetitively Inhibit Function of Four Distinct Nicotinic Acetylcholine Receptor Subtypes," J Pharmacol Exp Ther. 299(3):1038-48 (2001).
NCBI Reference SNP(refSNP) Cluster Report: rs60910145, <http://www.ncbi.nlm.nih.gov/projects/SNP/snp_ref.cgi?rs=60910145>, retrieved on Dec. 15, 2011 (3 pages).
International Search Report and Written Opinion of the International Searching Authority for International Application No. PCT/US12/39145, dated Dec. 7, 2012 (14 pages).
Office Action for Canadian Patent Application No. 2,668,652, dated Sep. 18, 2013 (4 pages).
International Preliminary Report on Patentability and Written Opinion for Itnernational Application No. PCT/US2009/001541, dated Sep. 14, 2010 (9 pages).
International Search Report for International Application No. PCT/US11/32924, dated Apr. 9, 2012 (6 pages).
NCBI Blast for Accession No. AAI43039.1. Retrieved on Jun. 9, 2015 (2 pages).
Vanhollebeke et al., "Distinct roles of haptoglobin-related protein and apolipoprotein L-I in trypanolysis by human serum," Proc Natl Acad Sci USA. 104(10):4118-23 (2007).
Office Action for Australian Patent Applicaion No. 2009223739, dated Aug. 9, 2013 (4 pages).
Freedman et al., "The apolipoprotein L1 (APOL1) gene and nondiabetic nephropathy in African Americans," J Am Soc Nephrol. 21(9):1-5 (2010).
Written Opinion for International Application No. PCT/US2010/41537, dated Oct. 18, 2010 (3 pages).
International Search Report and Written Opinion for International Application No. PCT/US13/70908, dated Apr. 23, 2014 (14 pages).
International Search Report of International Applciation No. PCT/US2010/41537, dated Oct. 18, 2010 (4 pages).
European Patent Office Communication for European Patent Applciation No. 11007950.6, dated Feb. 27, 2012 (14 pages).
Final Rejection for Japanese Patent Applciation No. 2009-537235, dated Oct. 1, 2013 (6 pages).
Office Action for U.S. Appl. No. 14/496,629, dated May 12, 2016 (20 pages).
D'Agati et al., "Focal segmental glomerulosclerosis," N Engl J Med. 365(25):2398-411 (2011).
"TRPV1-mediated impermeable sodium channel blocking drug inhibits pain receptor," Chin J Neuromed. 6(11):1171 (2007).
Extended European Search Report for European Patent Application No. 09718704.1, dated Dec. 11, 2012 (11 pages).
Office Action for Chinese Patent Application No. 200780050131.9, dated Feb. 23, 2011 (11 pages).
Ruparel et al., "Homologous and heterologous desensitization of capsaicin and mustard oil responses utilize different cellular pathways in nociceptors," Pain. 135(3):271-9 (2008).
Office Action for Australian Patent Application No. 2007322033, dated Apr. 23, 2012 (3 pages).
Kiberstis, "Letter and reviews from Science (1189125)," E-mail to Martin Pollak dated Mar. 16, 2010 (3 pages).

(56) References Cited

OTHER PUBLICATIONS

Kaufman, "Transgenic analysis of a 100-kb human beta-globin cluster-containing DNA fragment propagated as a bacterial artificial chromosome," Blood. 94(9):3178-84 (1999).
NCBI Blast for Accession No. NM_ 001136540.1. Retrieved on Jun. 9, 2015 (5 pages).
McCleskey, "Neuroscience: a local route to pain relief," Nature. 449(7162):545-6 (2007).
Shiyi, "Experimental study on analgesic effects of Epidural Capsaicin." Chin J Pain Med. 1(10):37-41 (2004). English Abstract Only.
Page et al., "Polymorphisms in the Apolipoprotein L1 gene and their effects on blood lipid and glucose levels in middle age males," Genes Nutr. 1(2):133-5 (2006).
European Patent Office Communication for European Patent Applciation No. 10797919.7, dated Oct. 29, 2012 (15 pages).
Snutch, "Targeting chronic and neuropathic pain: the N-type calcium channel comes of age," NeuroRx. 2(4):662-70 (2005).
Exetended European Search Report for European Patent Application No. 11007949.8, dated Oct. 11, 2012 (32 pages).
Bentley et al., "Variation in APOL1 Contributes to Ancestry-Level Differences in HDLc-Kidney Function Association," Int J Nephrol. 748984 (2012) (10 pages).
Wang et al., "Rapid analysis of gene expression (RAGE) facilitates universal expression profiling," Nucelic Acids Res. 27(23):4609-18 (1999).
Examination Report for Australian Patent Application No. 2010271269, dated Jun. 29, 2016 (3 pages).
Office Action for Chinese Patent Application No. 200780050131.9, dated Sep. 13, 2013 (7 pages).
Paul, "Genes linked to kidney disease," Genetics Abstract, <http://geneticabstracts.blogspot.com/2008/10/genes-linked-to-kidney-disease.html>, retrieved on Aug. 22, 2011 (2 pages).
Written Opinion of the International Searching Authority for International Application No. PCT/US2007/024174 (18 pages).
Yaksh, "Calcium channels as therapeutic targets in neuropathic pain," J Pain 7:S13-S30 (2006).
Office Action for U.S. Appl. No. 12/515,429, dated Apr. 27, 2011 (17 pages).
Li et al., "Distribution and effect of apoL-I genotype on plasma lipid and apolipoprotein levels in Chinese normalipidemic and endogenous hypertriglyceridemic subjects," Clin Chim Acta. 403(1-2):152-5 (2009).
NCBI Blast for Accession No. Z82215.1. Retrieved on Jun. 9, 2015 (31 pages).
Office Action for Chinese Patent Application No. 200780050131.9, dated Apr. 3, 2013 (8 pages).
International Preliminary Report on Patentability and Written Opinion for International Application No. PCT/US2013/070908, dated Jun. 11, 2015 (8 pages).
NCBI Blast for Accession No. NC_000022.10. Retrieved on Jun. 9, 2015 (2 pages).

Lecordier et al., "C-terminal mutants of apolipoprotein L-I efficiently kill both Trypanosoma brucei brucei and Trypanosoma brucei rhodesiense," PLoS Pathog 5(12):e1000685 1-11 (2009).
Office Action for Japanese Patent Application No. 2010-550687, dated Oct. 1, 2013 (6 pages).
Office Action for Chinese Patent Application No. 200780050131.9, dated Jun. 4, 2012 (10 pages).
Communication from European Patent Office for EP Application 10797919.7, dated Apr. 17, 2015 (7 pages).
Office Action for U.S. Appl. No. 12/515,249, dated Oct. 7, 2011 (21 pages).
Field et al., "Identification of the alpha2-delta-1 subunit of voltage-dependent calcium channels as a molecular target for pain mediating the analgesic actions of pregabalin," Proc Natl Acad Sci U S A. 103(46):17537-42 (2006).
Hartman et al., "Global changes in STAT target selection and transcription regulation upon interferon treatments," Genes Dev. 19(24):2953-68 (2005).
Vanhollebeke et al., "Human Trypanosoma evansi infection linked to a lack of apolipoprotein L-I," N Engl J Med. 355(26):2752-6 (2006).
NCBI Blast for Accession No. AAI42721.1. Retrieved on Jun. 9, 2015 (2 pages).
NCBI Blast for Accession No. NM_145343.2. Retrieved on Jun. 9, 2015 (5 pages).
Breznan et al., "The lipid composition of high-density lipoprotein affects its re-absorption in the kidney by proximal tubule epithelial cells," Biochem J. 379(Pt 2):343-9 (2004).
Appel et al., "Intensive blood-pressure control in hypertensive chronic kidney disease," N Engl J Med. 363(10): 918-29 (2010).
International Preliminary Report on Patentability and Written Opinion for International Appliction No. PCT/US2010/041537, dated Jan. 10, 2012 (7 pages).
Examiner's Report for Australian Patent Application No. 2010271269, dated Sep. 9, 2015 (4 pages).
Office Action for Canadian Patent Application No. 2,767,646, dated Apr. 11, 2016 (4 pages).
NCBI Blast for Accession No. NM_003661.3. Retrieved on Jun. 9, 2015 (5 pages).
Anger et al., "Medicinal chemistry of neuronal voltage-gated sodium channel blockers," J. Med. Chem. 44(2):115-137 (2001).
Page et al., "The human apolipoprotein L gene cluster: identification, classification, and sites of distribution," Genomics 74(1):71-8 (2001).
"Human apolipoprotein L1 (ApoL1) in cancer and chronic kidney disease," available in PMC Mar. 23, 2009, published in final edited form as: FEBS Lett. 586(7):947-55 (2012) (19 pages).
Lee et al., "Role of TRPV1 in inflammation-induced airway hypersensitivity," Curr Opin Phamacol. 9(3):243-9 (2009).
Fishman et al. "Intravenous Lidocaine for Treatment-resistant Pruritus," Am. J. Med. 102:584-585 (1997).
Steinhoff et al. "Neurological, Neuroimmunological, and Neuroendocrine Basis of Pruritus," J. Invest. Derm. 126:1705-1718 (2006).
Communication from European Patent Office for EP Application 11 007 949.9, dated Jun. 7, 2018 (6 pages).

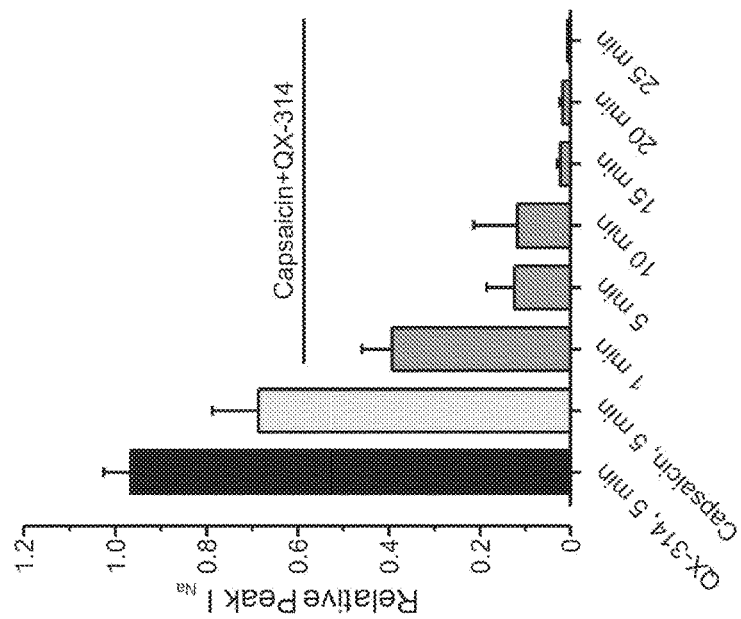
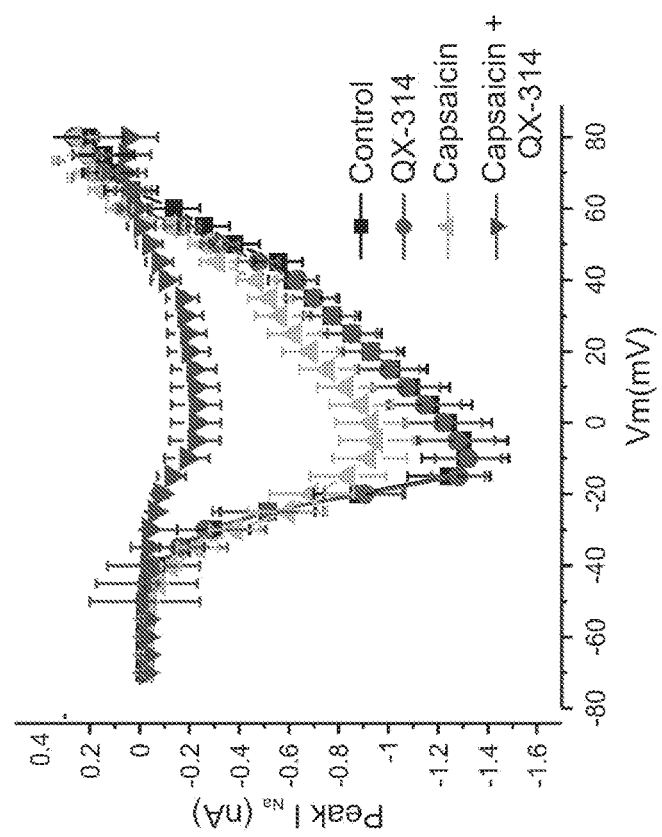

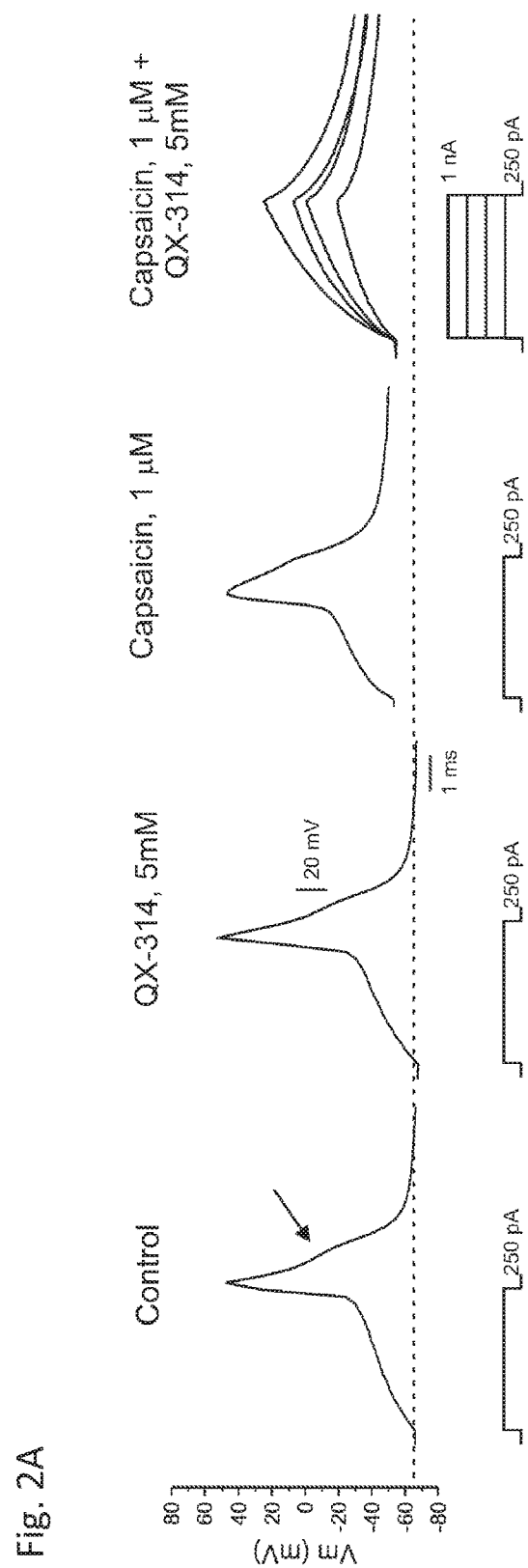

intraplantar injection

METHODS, COMPOSITIONS, AND KITS FOR TREATING PAIN AND PRURITIS

CROSS REFERENCE TO RELATED APPLICATIONS

This application is a continuation of, and claims priority to, U.S. patent application Ser. No. 14/496,629, now U.S. Pat. No. 9,603,817, filed Sep. 25, 2014, which is a continuation of, and claims priority to, U.S. patent application Ser. No. 12/515,429, filed Dec. 21, 2009, which is a national stage entry of International Patent Application No. PCT/US2007/024174, filed Nov. 19, 2007, which claims priority to U.S. Patent Application No. 60/997,510, filed Oct. 3, 2007; U.S. Patent Application No. 60/958,594, filed Jul. 6, 2007; and U.S. Patent Application No. 60/860,124, filed Nov. 20, 2006, the contents of each of which are incorporated herein by reference in their entirety.

BACKGROUND OF THE INVENTION

The invention features methods, compositions, and kits for selective inhibition of pain- and itch sensing neurons (nociceptors and pruriceptors) by drug molecules of small molecule weight, while minimizing effects on non-pain-sensing neurons or other types of cells. According to the method of the invention, small, hydrophilic drug molecules gain access to the intracellular compartment of pain-sensing neurons via entry through receptors that are present in pain- and itch-sensing neurons but to a lesser extent or not at all in other types of neurons or in other types of tissue.

Local anesthetics such as lidocaine and articaine act by inhibiting voltage-dependent sodium channels in neurons. These anesthetics block sodium channels and thereby the excitability of all neurons, not just pain-sensing neurons (nociceptors). Thus, while the goal of topical or regional anesthesia is to block transmission of signals in nociceptors to prevent pain, administration of local anesthetics also produces unwanted or deletrious effects such as general numbness from block of low threshold pressure and touch receptors, motor deficits from block of motor axons and other complications from block of autonomic fibers. Local anesthetics are relatively hydrophobic molecules that gain access to their blocking site on the sodium channel by diffusing into or through the cell membrane. Permanently-charged derivatives of these compounds (such as QX-314, a quaternary nitrogen derivative of lidocaine), which are not membrane-permeant, have no effect on neuronal sodium channels when applied to the external surface of the nerve membrane but can block sodium channels if somehow introduced inside the cell, for example by a micropipette used for whole-cell electrophysiological recording from isolated neurons. Pain-sensing neurons differ from other types of neurons in expressing (in most cases) the TRPV1 receptor/channel, activated by painful heat or by capsaicin, the pungent ingredient in chili pepper. Other types of receptors selectively expressed in various types of pain-sensing and itch-sensing (pruriceptor) neurons include but are not limited to TRPA1, TRPM8, and P2X(2/3) receptors.

Neuropathic, inflammatory, and nociceptive pain differ in their etiology, pathophysiology, diagnosis, and treatment. Nociceptive pain occurs in response to the activation of a specific subset of peripheral sensory neurons, the nociceptors, by intense or noxious stimuli. It is generally acute, self-limiting and serves a protective biological function by acting as a warning of potential or on-going tissue damage. It is typically well-localized. Examples of nociceptive pain include but are not limited to traumatic or surgical pain, labor pain, sprains, bone fractures, burns, bumps, bruises, injections, dental procedures, skin biopsies, and obstructions.

Inflammatory pain is pain that occurs in the presence of tissue damage or inflammation including postoperative, post-traumatic pain, arthritic (rheumatoid or osteoarthritis) pain and pain associated with damage to joints, muscle, and tendons as in axial low back pain.

Neuropathic pain is a common type of chronic, non-malignant pain, which is the result of an injury or malfunction in the peripheral or central nervous system and serves no protective biological function. It is estimated to affect more than 1.6 million people in the U.S. population. Neuropathic pain has many different etiologies, and may occur, for example, due to trauma, surgery, herniation of an intervertebral disk, spinal cord injury, diabetes, infection with herpes zoster (shingles), HIV/AIDS, late-stage cancer, amputation (including mastectomy), carpal tunnel syndrome, chronic alcohol use, exposure to radiation, and as an unintended side-effect of neurotoxic treatment agents, such as certain anti-HIV and chemotherapeutic drugs.

In contrast to nociceptive pain, neuropathic pain is frequently described as "burning," "electric," "tingling," or "shooting" in nature. It is often characterized by chronic allodynia (defined as pain resulting from a stimulus that does not ordinarily elicit a painful response, such as light touch) and hyperalgesia (defined as an increased sensitivity to a normally painful stimulus), and may persist for months or years beyond the apparent healing of any damaged tissues.

Pain may occur in patients with cancer, which may be due to multiple causes; inflammation, compression, invasion, metastatic spread into bone or other tissues.

There are some conditions where pain occurs in the absence of a noxious stimulus, tissue damage or a lesion to the nervous system, called dysfunctional pain and these include but are not limited to fibromyalgia, tension type headache, irritable bowel disorders and erythermalgia.

Migraine is a headache associated with the activation of sensory fibers innervating the meninges of the brain.

Itch (pruritus) is a dermatological condition that may be localized and generalized and can be associated with skin lesions (rash, atopic eczema, wheals). Itch accompanies many conditions including but not limited to stress, anxiety, UV radiation from the sun, metabolic and endocrine disorders (e.g., liver or kidney disease, hyperthyroidism), cancers (e.g., lymphoma), reactions to drugs or food, parasitic and fungal infections, allergic reactions, diseases of the blood (e.g., polycythemia vera), and dermatological conditions. Itch is mediated by a subset of small diameter primary sensory neurons, the pruriceptor, that share many features of nociceptor neurons, including but not limited to expression of TRPV1 channels. Certain itch mediators—such as eicosanoids, histamine, bradykinin, ATP, and various neurotrophins have endovanilloid functions. Topical capsaicin suppresses histamine-induced itch. Pruriceptors like nociceptors are therefore a suitable target for this method of delivering ion channels blockers.

Despite the development of a variety of therapies for pain and itch, there is a need for additional agents.

SUMMARY OF THE INVENTION

In a first aspect, the invention features a method for treating pain and itch (e.g., neuropathic pain, inflammatory pain, nociceptive pain, idiopathic pain, cancer pain, migraine, dysfunctional pain or procedural pain (e.g., dental procedures, injections, setting fractures, biopsies)) as well as pruritus in a patient by administering to the patient a first compound that inhibits one or more voltage-gated ion channels when applied to the internal face of the channels but does not substantially inhibit the channels when applied to the external face of the channels, wherein the first compound is capable of entering neurons through a membrane bound receptor/ion channel when the receptor is activated; and, optionally, a second compound that activates a receptor through which the first compound can pass. In certain embodiments, the second compound activates a receptor selected from TRPV1, P2X(2/3), TRPA1, and TRPM8 through which the first compound can pass. Treatment of pain or itch can be determined using any standard pain or itch index, such as those described herein, or can be determined based on the patient's subjective pain or itch assessment. A patient is considered "treated" if there is a reported reduction in pain or a reduced reaction to stimuli that should cause pain and a reduction in itch. In certain embodiments, it is desirable to administer the second compound in order to ensure that the receptors (e.g., the TRPV1, P2X(2/3), TRPA1, and/or TRPM8 receptors) are activated, thus allowing for entry of the first compound. In other embodiments, because the receptors (e.g., the TRPV1, P2X(2/3), TRPA1, and/or TRPM8 receptors) are already activated, the second compound is not administered. Consequently, the first compound enters only neurons having receptors that are endogenously activated. In still other embodiments, the receptors (e.g., the TRPV1, P2X(2/3), TRPA1, and/or TRPM8 receptors) are activated by indicing a physiological state that activates these receptors, thus allowing for entry of the first compound.

If desired, two or more compounds that activate TRPV1, P2X(2/3), TRPA1, and/or TRPM8 receptors can be employed, as can two or more compounds that inhibit one or more voltage-gated ion channels. Desirably, the first compound(s) and the second compound(s) are administered to the patient within 4 hours, 2 hours, 1 hour, 30 minutes, or 15 minutes of each other, or are administered substantially simultaneously. Importantly, either compound can be administered first. Thus, in one embodiment, one or more compounds that activate TRPV1, P2X(2/3), TRPA1, and/or TRPM8 receptors are administered first, while in another embodiment, one or more compounds that inhibit one or more voltage-gated ion channels when applied to the internal face of the channels but do not substantially inhibit the channels when applied to the external face of the channels are administered first. The compounds can be co-formulated into a single composition or can be formulated separately. Each of the compounds can be administered, for example, by oral, parenteral, intravenous, intramuscular, rectal, cutaneous, subcutaneous, topical, transdermal, sublingual, nasal, vaginal, intrathecal, epidural, or ocular administration, or by injection, inhalation, or direct contact with the nasal or oral mucosa.

Activators of TRPV1 receptors include but are not limited to capsaicin, eugenol arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), C18 N-acylethanolamines, lipoxygenase derivatives such as 12-hydroperoxyeicosatetraenoic acid, inhibitor cysteine knot (ICK) peptides (vanillotoxins), piperine, MSK195 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-alpha-sanshool, 2-aminoethoxydiphenyl borate, 10-shogaol, oleylgingerol, oleylshogaol, and SU200 (N-(4-tert-butyl-benzyl)-N'-(4-hydroxy-3-methoxybenzyl)thiourea). Other activators of TRPV1 receptors are described in O'Dell et al., Bioorg Med Chem (2007) 15:6164-6149, and Sexton et al., FASEB J (2007) 21:2695-2703.

Activators of TRPA1 receptors include but are not limited to cinnamaldehyde, allyl-isothiocynanate, diallyl disulfide, icilin, cinnamon oil, wintergreen oil, clove oil, acrolein, hydroxy-alpha-sanshool, 2-aminoethoxydiphenyl borate, 4-hydroxynonenal, methyl p-hydroxybenzoate, mustard oil, and 3'-carbamoylbiphenyl-3-yl cyclohexylcarbamate (URB597). Other activators of TRPA1 receptors are described in Taylor-Clark et al., Mol Pharmacol (2007) PMID: 18000030; Macpherson et al., Nature (2007) 445:541-545; and Hill et al., J Biol Chem (2007) 282:7145-7153.

Activators of P2X receptors include but are not limited to ATP, 2-methylthio-ATP, 2' and 3'-O-(4-benzoylbenzoyl)-ATP, and ATP5'-O-(3-thiotriphosphate).

Activators of TRPM8 receptors include but are not limited to menthol, icilin, eucalyptol, linalool, geraniol, and hydroxycitronellal.

In certain embodiments, the first compound inhibits voltage-gated sodium channels. Exemplary inhibitors of this class are QX-314, N-methyl-procaine, QX-222, N-octylguanidine, 9-aminoacridine, and pancuronium.

In yet other embodiments, the first compound inhibits voltage-gated calcium channels. Exemplary inhibitors of this class are D-890 (quaternary methoxyverapamil) and CERM 11888 (quaternary bepridil).

In still other embodiments, the first compound is a quarternary amine derivative or other charged derivative of a compound selected from riluzole, mexilitine, phenytoin, carbamazepine, procaine, articaine, bupivicaine, mepivicaine, tocainide, prilocaine, diisopyramide, bencyclane, quinidine, bretylium, lifarizine, lamotrigine, flunarizine, and fluspirilene. Exemplary derivatives are described herein.

The invention also features a quarternary amine derivative or other charged derivative of a compound selected from riluzole, mexilitine, phenytoin, carbamazepine, procaine, articaine, bupivicaine, mepivicaine, tocainide, prilocaine, diisopyramide, bencyclane, quinidine, bretylium, lifarizine, lamotrigine, flunarizine, and fluspirilene.

In a related aspect, the invention features a pharmaceutical composition that includes a quarternary amine derivative or other charged derivative of a compound selected from riluzole, mexilitine, phenytoin, carbamazepine, procaine, articaine, bupivicaine, mepivicaine, tocainide, prilocaine, diisopyramide, bencyclane, quinidine, bretylium, lifarizine, lamotrigine, flunarizine, and fluspirilene, and a pharmaceutically acceptable excipient.

The invention also features a composition that includes: (i) a first compound that activates a receptor selected from TRPV1, P2X(2/3), TRPA1, and TRPM8; and (ii) a second compound that inhibits one or more voltage-gated ion channels when applied to the internal face of these channels but does not substantially inhibit the channels when applied to their external face, wherein the second compound is capable of entering pain sensing neurons through TRPV1, P2X(2/3), TRPA1, and/or TRPM8 receptors when these receptors are activated. In one embodiment, the second compound is reduced in activity or partially active when applied to the external face, but more active when applied to the internal face. The composition can be formulated, for example, for oral, intravenous, intramuscular, rectal, cutaneous, subcutaneous, topical, transdermal, sublingual, nasal, vaginal, intrathecal, epidural, or ocular administration, or by injection, inhalation, or direct contact with the nasal or oral mucosa. If desired, the composition can contain two or more compounds that activate TRPV1, P2X(2/3), TRPA1, and/or TRPM8 receptors, and/or two or more compound that inhibits one or more voltage-gated ion channels.

The invention also features a method for inhibiting one or more voltage-gated ion channels in a cell by contacting the cell with: (i) a first compound that activates a receptor selected from TRPV1, P2X(2/3), TRPA1, and TRPM8; and (ii) a second compound that inhibits one or more voltage-gated ion channels when applied to the internal face of the channels but does not substantially inhibit the channels when applied to the external face of the channels, wherein said second compound is capable of entering pain sensing neurons through the receptor when the receptor is activated. Suitable compounds are provided above.

The invention also features a method for identifying a compound as being useful for the treatment of pain and itch. This method includes the steps of: (a) contacting the external face of TRPV1, TRPA1, TRPM8, and/or P2X(2/3)-expressing neurons with: (i) a first compound that activates TRPV1 TRPA1, TRPM8 or P2X(2/3) receptors; and (ii) a second compound that inhibits one or more voltage-gated ion channels when applied to the internal face of the channels but does not substantially inhibit the channels when applied to the external face of the channels, and (b) determining whether the second compound inhibits the voltage-gated ion channels in the neurons. Inhibition of voltage-gated ion channels by the second compound identifies the second compound as a compound that is useful for the treatment of pain and/or itch.

The methods, compositions, and kits can also be used to selectively block neuronal activity in other types of neurons that express different members of the TRPV, TRPA, TRPM, and P2X receptor families, where the first compound is an agonist of the particular TRPV, TRPA, TRPM, and P2X receptor present in those types of neurons, and the second compound is a sodium or calcium channel blocker that is normally membrane impermeant.

It is understood that other receptors may exist that would permit the entry of compounds that would otherwise be incapable of entering. Co-administration of compounds that activate one or more of these receptors in combination with one or more compounds that inhibit one or more voltage-gated ion channels when applied to the internal face of the channels but does not substantially inhibit the channels when applied to the external face of the channels is also an aspect of the invention.

The methods, compositions, and kits of the invention allow for a block of pain or itch without altering light touch or motor control. For example, patients receiving an epidural will not have a complete loss of sensory input.

The term "pain" is used herein in the broadest sense and refers to all types of pain, including acute and chronic pain, such as nociceptive pain, e.g. somatic pain and visceral pain; inflammatory pain, dysfunctional pain, idiopathic pain, neuropathic pain, e.g., centrally generated pain and peripherally generated pain, migraine, and cancer pain.

The term "nociceptive pain" is used to include all pain caused by noxious stimuli that threaten to or actually injure body tissues, including, without limitation, by a cut, bruise, bone fracture, crush injury, burn, and the like. Pain receptors for tissue injury (nociceptors) are located mostly in the skin, musculoskeletal system, or internal organs.

The term "somatic pain" is used to refer to pain arising from bone, joint, muscle, skin, or connective tissue. This type of pain is typically well localized.

The term "visceral pain" is used herein to refer to pain arising from visceral organs, such as the respiratory, gastrointestinal tract and pancreas, the urinary tract and reproductive organs. Visceral pain includes pain caused by tumor involvement of the organ capsule. Another type of visceral pain, which is typically caused by obstruction of hollow viscus, is characterized by intermittent cramping and poorly localized pain. Visceral pain may be associated with inflammation as in cystitis or reflux esophagitis.

The term inflammatory pain includes pain associates with active inflammation that may be caused by trauma, surgery, infection and autoimmune diseases.

The term "neuropathic pain" is used herein to refer to pain originating from abnormal processing of sensory input by the peripheral or central nervous system consequent on a lesion to these systems.

The term "procedural pain" refers to pain arising from a medical, dental or surgical procedure wherein the procedure is usually planned or associated with acute trauma.

The term "itch" is used herein in the broadest sense and refers to all types of itching and stinging sensations localized and generalized, acute intermittent and persistent. The itch may be idiopathic, allergic, metabolic, infectious, drug-induced, due to liver, kidney disease, or cancer. "Pruritus" is severe itching.

By "patient" is meant any animal. In one embodiment, the patient is a human. Other animals that can be treated using the methods, compositions, and kits of the invention include but are not limited to non-human primates (e.g., monkeys, gorillas, chimpaneees), domesticated animals (e.g., horses, pigs, goats, rabbits, sheep, cattle, llamas), and companion animals (e.g., guinea pigs, rats, mice, lizards, snakes, dogs, cats, fish, hamsters, and birds).

Compounds useful in the invention include but are not limited to those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein.

By "low molecular weight" is meant less than about 500 Daltons.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include but are not limited to acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include but are not limited to sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups.

By "$C_{1-4}$ alkyl" is meant a a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "$C_{2-4}$ alkenyl" is meant a branched or unbranched hydrocarbon group containing one or more double bonds and having from 2 to 4 carbon atoms. A $C_{2-4}$ alkenyl may optionally include monocyclic or polycyclic rings, in which each ring desirably has from three to six members. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "$C_{2-4}$ alkynyl" is meant a branched or unbranched hydrocarbon group containing one or more triple bonds and having from 2 to 4 carbon atoms. A $C_{2-4}$ alkynyl may optionally include monocyclic, bicyclic, or tricyclic rings, in which each ring desirably has five or six members. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups. Examples of $C_{1-7}$ heteroalkyls include, without limitation, methoxymethyl and ethoxyethyl.

By "halide" is meant bromine, chlorine, iodine, or fluorine.

By "fluoroalkyl" is meant an alkyl group that is substituted with a fluorine atom.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^{+}$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl, heteroalkyl, heteroaryl, and/or aryl groups, resulting in a positive charge at the nitrogen atom.

By "charged moiety" is meant a moiety which gains a proton at physiological pH thereby becoming positively charged (e.g., ammonium, guanidinium, or amidinium) or a moiety that includes a net formal positive charge without protonation (e.g., quaternary ammonium). The charged moiety may be either permanently charged or transiently charged.

As used herein, the term "parent" refers to a channel blocking compound which can be modified by quaternization or guanylation of an amine nitrogen atom present in the parent compound. The quaternized and guanylated compounds are derivatives of the parent compound. The guanidyl derivatives described herein are presented in their uncharged base form. These compounds can be administered either as a salt (i.e., an acid addition salt) or in their uncharged base form, which undergoes protonation in situ to form a charged moiety.

Other features and advantages of the invention will be apparent from the following detailed description, and from the claims.

BRIEF DESCRIPTION OF THE DRAWING

FIGS. 1A, 1B, and 1C show that the co-application of extracellular QX-314 (5 mM) and capsaicin (1 µM) selectively blocks sodium currents in capsaicin-responsive dorsal root ganglion (DRG) sensory neurons. FIG. 1A (left) shows the effect on sodium current (elicited by a step to from −70 to −5 mV) of 10 minutes wash-in of 5 mM QX-314 alone (red trace), 1 µM capsaicin alone (green trace), and co-applied 5 mM QX-314 and 1 µM capsaicin (blue trace) in a small (24 µm) capsaicin-sensitive adult cultured DRG neuron. Top panel: Brief application of capsaicin induced a prolonged inward current (holding voltage of −70 mV) in this neuron. FIG. 1A (right) also shows the effect on sodium current of the same series of drug applications on a large (52 µm) capsaicin-insensitive neuron. FIG. 1B shows peak inward current as a function of test pulse recorded in control (black symbols), in the presence of 5 mM QX-314 alone (red symbols), 1 µM capsaicin alone (green symbols), and co-applied 5 mM QX-314 and 1 µM capsaicin (blue symbols). Symbols show mean±SEM for experiments on 25 small capsaicin-sensitive neurons. Currents were elicited by 20 ms depolarizing steps from a holding potential of −70 mV to a range of test potentials in 5 mV increments. FIG. 1C shows a time course of the effect of combination of capsaicin and QX-314 on peak sodium current. Bars plot mean±SEM for peak sodium current normalized relative to that in control (n=25).

FIGS. 2A and 2B show that the co-application of QX-314 and capsaicin blocks excitability in nociceptive-like DRG neurons. FIG. 2A shows that a depolarizing current step (250 pA, 4 ms) applied to a small (23 µm) DRG neuron evoked a nociceptor-like broad action potential with a prominent deflection on the falling phase (arrow). 2 minutes wash-in of QX-314 (5 mM) had no effect (second panel). Capsaicin (1 µM) reduced the action potential amplitude (third panel), probably due to a combination of the modest reduction of sodium current produced by capsaicin as in FIG. 1 and inactivation of sodium current secondary to the depolarization produced by capsaicin. Co-applied QX-314 and capsaicin completely abolished action potential generation even with much larger stimulating current injection. FIG. 2B shows the mean±SEM of action potential amplitudes (n=25 for QX-314, n=15 for capsaicin and capsaicin+QX-314).

FIG. 3A shows the mechanical threshold for paw withdrawal in response to von Frey hairs of increasing strength after interplantar injection of QX-314 alone (2%, 10 µL; green symbols), capsaicin alone (10 µg/10 µL; black symbols), or QX-314 and capsaicin applied together (red symbols). Number of animals that did not respond at all to the highest value (57 g, arrow) is indicated for time points with largest effects. (*=p<0.05, n=6 for each group). FIG. 3B shows the same for thermal (radiant heat) threshold for paw withdrawal. Arrow indicates cutoff, and numbers of animals not responding to strongest stimulus is indicated for time points with largest effects. (*=p<0.05, n=6 for each group).

FIG. 4A shows the mechanical threshold for paw withdrawal in response to von Frey filaments of increasing strength after sciatic injection of QX-314 alone (0.2%, 100 µL), capsaicin alone (0.5 µg/µL, 100 µL), or QX-314 injected 10 minutes before capsaicin. Number of animals that did not respond at all to the highest value (57 g, arrow) is indicated for time points with largest effects. (*=p<0.05, **=p<0.01, n=6 for each group). FIG. 4B shows the same for thermal (radiant heat) threshold for paw withdrawal. FIG. 4C shows the change in motor function (score: 2=full paralysis; 1=partial paralysis; 0=no impairment) evaluated after sciatic injection of lidocaine (2%; 0.2%), QX-314 (0.2%), capsaicin (5 µg/10 µL) and QX-314 followed by capsaicin injection. Numbers of animals affected by the injections are indicated above each column.

DETAILED DESCRIPTION OF THE INVENTION

Figure 1A:
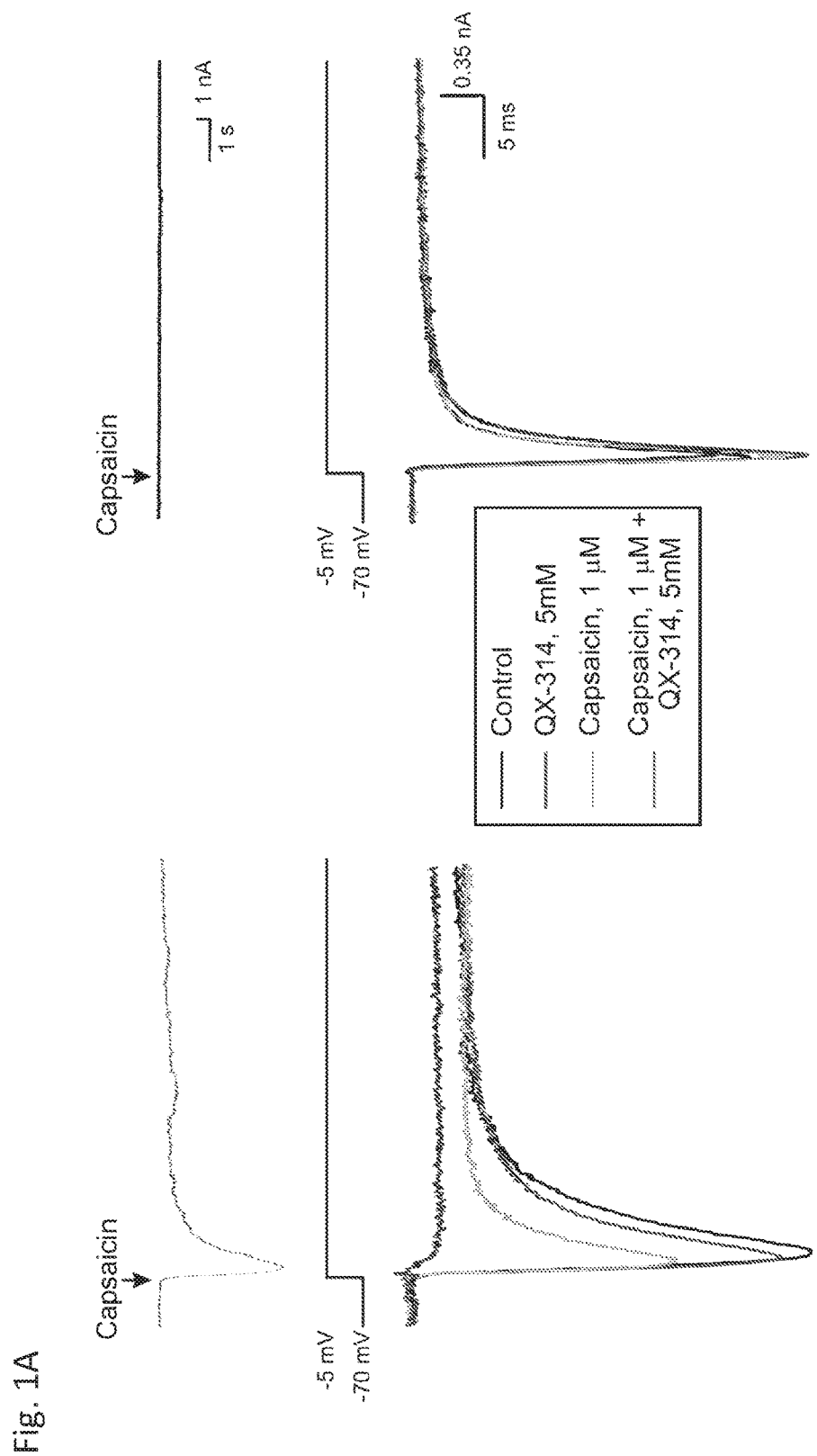

Voltage-dependent ion channels in pain-sensing neurons are currently of great interest in developing drugs to treat pain. Blocking voltage-dependent sodium channels in pain-sensing neurons can block pain signals by interrupting initiation and transmission of the action potential, and blocking calcium channels can prevent neurotransmission of the pain signal to the second order neuron in the spinal cord. Heretofore, a limitation in designing small organic molecules that block sodium channels or calcium channels is that they must be active when applied externally to the target cell. The vast majority of such externally-applied molecules are hydrophobic and can pass through membranes. Because of this, they will enter all cells and thus have no selectivity for affecting only pain-sensing neurons. Yet, some blockers are known, such as QX-314, that are only effective when present inside the cell. To date, such blockers have been studied primarily with electrophysiological recording techniques such as whole-cell patch clamp that permit dialysis of the inside of a cell by mechanical rupturing of the membrane. The difficulty of mechanical rupturing without killing the cell, and the difficulty of reversibly applying blockers inside the cell subsequently, has precluded development of high-throughput screening assays for drug molecules that might act from inside cells.

We have discovered a means for delivering inhibitors of voltage-gated ion channels into nociceptive neurons. By providing a way for these inhibitors to enter nociceptive neurons, the invention permits the use—both in screening and in therapy—of entire classes of molecules that are active as drug blockers from the inside of cell but need not be membrane-permeant. Moreover, confining the entry of such blockers to pain-sensing neurons under therapeutic conditions allows for the use of drugs that do not necessarily have intrinsic selectivity for ion channels in pain-sensing neurons compared to other types of cells, but rather gain their selective action on pain-sensing neurons by being allowed to enter pain-sensing neurons in preference to other cells in the nervous and cardiovascular system. Additionally, since TRPV1 receptors in particular are often more active in tissue conditions associated with pain (such as inflammation), entry is favored to the particular sensory neurons most associated with tissues that are generating pain. Itch-sensitive primary sensory neurons also express TRP channels, particularly TRPV1, and are also be amenable to this approach.

The invention is described in more detail below.

Inhibitors of Voltage-Gated Ion Channels

Inhibitors of voltage-gated ion channels that are suitable for use in the methods, compositions, and kits of the invention are desirably positively-charged, hydrophilic compounds. In one embodiment, the compounds are permanently charged (i.e., have a charge that is not transient). In another embodiment, the compounds are transiently charged. Suitable inhibitors of voltage-gated sodium channels include but are not limited to QX-314, N-methyl-procaine, QX-222, N-octyl-guanidine, 9-aminoacridine, and pancuronium. Suitable inhibitors of voltage-gated calcium channels include but are not limited to D-890 (quaternary methoxyverapamil) and CERM 11888 (quaternary bepridil).

Additionally, there are many known inhibitors of voltage-gated ion channels that would be of a suitable size to be useful in the methods of the invention (e.g., from about 100 to 4,000 Da, 100 to 3,000 Da, 100 to 2,000 Da, 150 to 1,500 Da, or even 200 to 1,200 Da) and that have amine groups, or can be modified to contain amine groups, that can be readily modified to be charged (e.g., as positively-charged quarternary amines, or as transiently charged guanylated compounds). Such inhibitors include but are not limited to riluzole, mexilitine, phenytoin, carbamazepine, procaine, tocainide, prilocaine, diisopyramide, bencyclane, quinidine, bretylium, lifarizine, lamotrigine, flunarizine, articaine, bupivicaine, mepivicaine, and fluspirilene.

Compounds that can be used in the compositions, kits, and methods of the invention include compounds of formulas I-X, below.

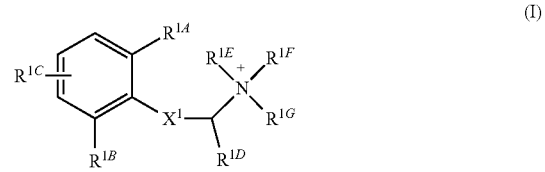

(I)

In formula I, each of $R^{1A}$, $R^{1B}$, and $R^{1C}$ is, independently, selected from H, halogen, $C_{1-4}$ alkyl, $C_{2-4}$ alkenyl, $C_{2-4}$ alkynyl, $OR^{1H}$, $NR^{1I}R^{1J}$, $NR^{1K}C(O)R^{1L}$, $S(O)R^{1M}$, $SO_2R^{1N}R^{1O}$, $SO_2NR^{1P}R^{1Q}$, $SO_3R^{1R}$, $CO_2R^{1S}$, $C(O)R^{1T}$, and $C(O)NR^{1U}R^{1V}$; and each of $R^{1H}$, $R^{1I}$, $R^{1J}$, $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, and $R^{1V}$ is, independently, selected from from H, $C_{1-4}$ alkyl, $C_{2-4}$ alkenyl, $C_{2-4}$ alkynyl, and $C_{2-4}$ heteroalkyl $X^1$ is selected from —$CR^{1W}R^{1X}$—, —$NR^{1Y}C(O)$—, —$OC(O)$—, —$SC(O)$—, —$C(O)NR^{1Z}$—, —$CO_2$—, and —$OC(S)$—; and each of $R^{1W}$, $R^{1X}$, $R^{1Y}$, and $R^{1Z}$ is, independently, selected from H, $C_{1-4}$ alkyl, $C_{2-4}$ alkenyl, $C_{2-4}$ alkynyl, and $C_{2-4}$ heteroalkyl; $R^{1D}$ is selected from H, $C_{1-4}$ alkyl, $C_{2-4}$ alkenyl, $C_{2-4}$ alkynyl, and $C_{2-4}$ heteroalkyl; and each of $R^{1E}$, $R^{1F}$, and $R^{1G}$ is, independently, selected from $C_{1-4}$ alkyl, $C_{2-4}$ alkenyl, $C_{2-4}$ alkynyl, and $C_{2-4}$ heteroalkyl; or $R^{1D}$ and $R^{1G}$ together complete a heterocyclic ring having at least one nitrogen atom. In a preferred embodiment, $X^1$ is —NHC(O)—. Exemplary compounds of formula I include methylated quaternary ammonium derivatives of anesthetic drugs, such as N-methyl lidocaine, N,N-dimethyl prilocaine, N,N,N-trimethyl tocainide, N-methyl etidocaine, N-methyl ropivacaine, N-methyl bupivacaine, N-methyl levobupivacaine, N-methyl mepivacaine. These derivatives can be prepared using methods analogous to those described in Scheme 1. Compounds of formula I include QX-314 (CAS 21306-56-9) and QX-222 (CAS 21236-55-5) (below).

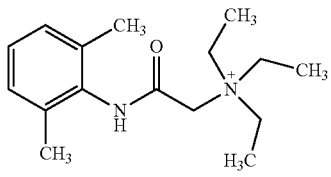

QX-314

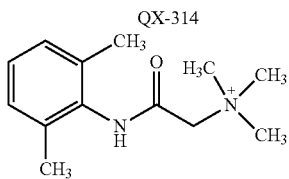

QX-222

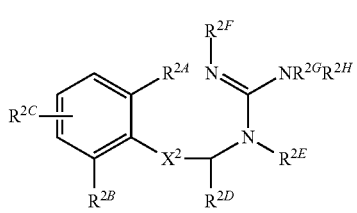

(II)

In formula II, each of $R^{2A}$, $R^{2B}$, and $R^{2C}$ is, independently, selected from H, halogen, $C_{1-4}$ alkyl, $C_{2-4}$ alkenyl, $C_{2-4}$ alkynyl, $OR^{2I}$, $NR^{2J}R^{2K}$, $NR^{2L}C(O)R^{2M}$, $S(O)R^{2N}$, $SO_2R^{2O}R^{2P}$, $SO_2NR^{2Q}R^{2R}$, $SO_3R^{2S}$, $CO_2R^{2T}$, $C(O)R^{2U}$, and $C(O)NR^{2V}R^{2W}$; and each of $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, $R^{2V}$, $R^{2W}$ is, independently, selected from H, $C_{1-4}$ alkyl, $C_{2-4}$ alkenyl, $C_{2-4}$ alkynyl, and $C_{2-4}$ heteroalkyl; $X^2$ is selected from —$CR^{2X}R^{2Y}$—, —$NR^{2Z}C(O)$—, —$OC(O)$—, —$SC(O)$—, —$C(O)NR^{2AA}$—, —$CO_2$—, and —$OC(S)$—; and each of $R^{2X}$, $R^{2Y}$, $R^{2Z}$, and $R^{2AA}$ is, independently, selected from H, $C_{1-4}$ alkyl, $C_{2-4}$ alkenyl, $C_{2-4}$ alkynyl, and $C_{2-4}$ heteroalkyl; $R^{2D}$ is selected from H, $C_{1-4}$ alkyl, $C_{2-4}$ alkenyl, $C_{2-4}$ alkynyl, and $C_{2-4}$ heteroalkyl; $R^{2E}$ is H or $C_{1-4}$ alkyl; and each of $R^{2F}$, $R^{2G}$, and $R^{2H}$ is, independently, selected from H, $C_{1-4}$ alkyl, $C_{2-4}$ alkenyl, $C_{2-4}$ alkynyl, and $C_{2-4}$ heteroalkyl; or $R^{2F}$ and $R^{2G}$ together complete a heterocyclic ring having two nitrogen atoms. Where $R^{2F}$ and $R^{2G}$ form a heterocyclic ring having two nitrogen atoms, the resulting guanidine group is, desirably, selected from

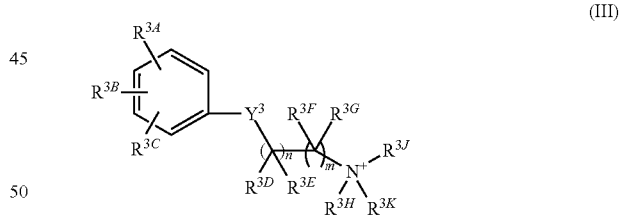

where $R^{2H}$ is H or $CH_3$. Desirably, $R^{2F}$ and $R^{2G}$ combine to form an alkylene or alkenylene of from 2 to 4 carbon atoms, e.g., ring systems of 5, 6, and 7-membered rings. In a preferred embodiment, $X^2$ is —NHC(O)—. Exemplary compounds of formula II include N-guanidyl derivatives (e.g., —$C(NH)NH_2$ derivatives) of anesthetic drugs, such as desethyl-N-guanidyl lidocaine, N-guanidyl prilocaine, N-guanidyl tocainide, desethyl-N-guanidyl etidocaine, desbutyl-N-guanidyl ropivacaine, desbutyl-N-guanidyl bupivacaine, desbutyl-N-guanidyl levobupivacaine, desmethyl-N-guanidyl mepivacaine. These derivatives can be prepared using methods analogous to those described in Schemes 2-5.

The guanidyl derivatives described herein (e.g., the compounds of formula II) are presented in their uncharged base form. These compounds can be administered either as a salt (i.e., an acid addition salt) or in their uncharged base form, which undergoes protonation in situ to form a charged moiety.

The synthesis of parent drugs of formulas I and II are described in the literature. See, for example, U.S. Pat. No. 2,441,498 (synthesis of lidocaine), U.S. Pat. No. 3,160,662 (synthesis of prilocaine), DE Pat. No. 2235745 (synthesis of tocainide), DE Pat. No. 2162744 (synthesis of etidocaine), PCT Publication No. WO85/00599 (synthesis of ropivacaine), U.S. Pat. No. 2,955,111 (synthesis of bupivacaine and levobupivacaine), and U.S. Pat. No. 2,799,679 (synthesis of mepivacaine).

(III)

In formula III, n=0-3 and m=0-3, with (n+m)=0-6; each of $R^{3A}$, $R^{3B}$, and $R^{3C}$ is, independently, selected from H, halogen, $C_{1-4}$ alkyl, $C_{2-4}$ alkenyl, $C_{2-4}$ alkynyl, $C_{2-4}$ heteroalkyl, $OR^{3L}$, $NR^{3M}R^{3N}$, $NR^{3O}C(O)R^{3P}$, $S(O)R^{3Q}$, $SO_2R^{3R}R^{3S}$, $SO_2NR^{3T}R^{3U}$, $SO_3R^{3V}$, $CO_2R^{3W}$, $C(O)R^{3X}$, and $C(O)NR^{3Y}R^{3Z}$; and each of $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, $R^{3W}$, $R^{3X}$, $R^{3Y}$, $R^{3Z}$ is, independently, selected from H, $C_{1-4}$ alkyl, $C_{2-4}$ alkenyl, $C_{2-4}$ alkynyl, and $C_{2-4}$ heteroalkyl; $Y^3$ is selected from from —$CR^{3AA}R^{3AB}$—, —$NR^{3AC}C(O)$—, —$OC(O)$—, —$SC(O)$—, —$C(O)NR^{3AD}$—, —$CO_2$—, and —$OC(S)$—; and each of $R^{3AA}$, $R^{3AB}$, $R^{3AC}$, and $R^{3AD}$ is, independently, selected from H, $C_{1-4}$ alkyl, $C_{2-4}$ alkenyl, $C_{2-4}$ alkynyl, and $C_{2-4}$ heteroalkyl; each of $R^{3D}$, $R^{3E}$, $R^{3F}$, and $R^{3G}$ is, independently, selected from H, $C_{1-4}$ alkyl, $C_{2-4}$ alkenyl, $C_{2-4}$ alkynyl, $C_{2-4}$ heteroalkyl, $C_{2-6}$ heterocyclyl, $C_{6-12}$ aryl, $C_{7-14}$ alkaryl, and $C_{3-10}$ alkheterocyclyl; each of $R^{3H}$, $R^{3J}$, and $R^{3K}$ is, independently, selected from $C_{1-4}$ alkyl, $C_{2-4}$ alkenyl, $C_{2-4}$ alkynyl, and $C_{2-4}$ heteroalkyl. The quaternary nitrogen in formula III is identified herein as N'. Exemplary compounds of formula III include methylated quaternary ammonium derivatives of anesthetic drugs, such as N'-methyl procaine, N'-methyl proparacaine, N'-methyl allocain, N'-methyl encainide, N'-methyl procainamide, N'-methyl metoclopramide, N'-methyl stovaine, N'-methyl propoxycaine, N'-methyl chloroprocaine, N',N'-dimethyl flecainide, and N'-methyl tetracaine. These derivatives can be prepared using methods analogous to those described in Scheme 1.

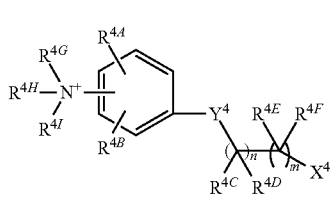

(IV)

In formula IV, n=0-3 and m=0-3, with (n+m)=0-6; each of $R^{4A}$ and $R^{4B}$ is, independently, selected from H, halogen, $C_{1-4}$ alkyl, $C_{2-4}$ alkenyl, $C_{2-4}$ alkynyl, $C_{2-4}$ heteroalkyl, $OR^{4L}$, $NR^{4M}R^{4N}$, $NR^{4O}C(O)R^{4P}$, $S(O)R^{4Q}$, $SO_2R^{4R}R^{4S}$, $SO_2NR^{4T}R^{4U}$, $SO_3R^{4V}$, $CO_2R^{4W}$, $C(O)R^{4X}$, and $C(O)NR^{4Y}R^{4Z}$; and each of $R^{4L}$, $R^{4M}R^{4N}$, $R^{4O}$, $R^{4P}$, $R^{4Q}$, $R^{4R}$, $R^{4S}$, $R^{4T}$, $R^{4U}$, $R^{4V}$, $R^{4W}$, $R^{4X}$, $R^{4Y}$, and $R^{4Z}$ is, independently, selected from H, $C_{1-4}$ alkyl, $C_{2-4}$ alkenyl, $C_{2-4}$ alkynyl, and $C_{2-4}$ heteroalkyl; $Y^4$ is selected from —$CR^{4AA}R^{4AB}$—, —$NR^{4AC}C(O)$—, —$OC(O)$—, —$SC(O)$—, —$C(O)NR^{4AD}$—, —$CO_2$—, and —$OC(S)$—; and each of $R^{4AA}$, $R^{4AB}$, $R^{4AC}$, and $R^{4AD}$ is, independently, selected from H, $C_{1-4}$ alkyl, $C_{2-4}$ alkenyl, $C_{2-4}$ alkynyl, and $C_{2-4}$ heteroalkyl; each of $R^{4C}$, $R^{4D}$, $R^{4E}$, and $R^{4F}$ is, independently, selected from H, $C_{1-4}$ alkyl, $C_{2-4}$ alkenyl, $C_{2-4}$ alkynyl, $C_{2-4}$ heteroalkyl, $C_{2-6}$ heterocyclyl, $C_{6-12}$ aryl, $C_{7-14}$ alkaryl, and $C_{3-10}$ alkheterocyclyl; $X^4$ is selected from H, $C_{1-4}$ alkyl, $C_{2-4}$ alkenyl, $C_{2-4}$ alkynyl, and $NR^{4J}R^{4K}$; each of $R^{4J}$ and $R^{4K}$ is, independently, selected from H, $C_{1-4}$ alkyl, $C_{2-4}$ alkenyl, $C_{2-4}$ alkynyl, and $C_{2-4}$ heteroalkyl; and each of $R^{4G}$, $R^{4H}$ and $R^{4I}$ is, independently, selected from $C_{1-4}$ alkyl, $C_{2-4}$ alkenyl, $C_{2-4}$ alkynyl, and $C_{2-4}$ heteroalkyl. The quaternary nitrogen in formula IV is identified herein as N'''. Exemplary compounds of formula III include methylated quaternary ammonium derivatives of anesthetic drugs, such as N''',N''',N'''-trimethyl procaine, N''',N''',N'''-trimethyl proparacaine, N''',N''',N'''-trimethyl procainamide, N''',N''',N'''-trimethyl metoclopramide, N''',N''',N'''-trimethyl propoxycaine, N''',N''',N'''-trimethyl chloroprocaine, N''',N''',N'''-dimethyl tetracaine, N''',N''',N'''-trimethyl benzocaine, and N''',N''',N'''-trimethyl butamben. These derivatives can be prepared using methods analogous to those described in Scheme 1.

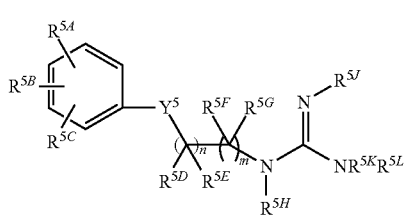

(V)

In formula V, n=0-3 and m=0-3, with (n+m)=0-6; each of $R^{5A}$, $R^{5B}$, and $R^{5C}$ is, independently, selected from H, halogen, $C_{1-4}$ alkyl, $C_{2-4}$ alkenyl, $C_{2-4}$ alkynyl, $C_{2-4}$ heteroalkyl, $OR^{5M}$, $NR^{5N}R^{5O}$, $NR^{5P}C(O)R^{5Q}$, $S(O)R^{5R}$, $SO_2R^{5S}R^{5T}$, $SO_2NR^{5U}R^{5V}$, $SO_3R^{5W}$, $CO_2R^{5X}$, $C(O)R^{5Y}$, and $C(O)NR^{5Z}R^{5AA}$; and each of $R^{5M}$, $R^{5N}$, $R^{5O}$, $R^{5P}$, $R^{5Q}$, $R^{5R}$, $R^{5S}$, $R^{5T}$, $R^{5U}$, $R^{5V}$, $R^{5W}$, $R^{5X}$, $R^{5Y}$, $R^{5Z}$, and $R^{5AA}$ is, independently, selected from H, $C_{1-4}$ alkyl, $C_{2-4}$ alkenyl, $C_{2-4}$ alkynyl, and $C_{2-4}$ heteroalkyl; $Y^5$ is selected from —$CR^{5AB}R^{5AC}$—, —$NR^{5AD}C(O)$—, —$OC(O)$—, —$SC(O)$—, —$C(O)NR^{5AE}$—, —$CO_2$—, and —$OC(S)$—; and each of $R^{5AB}$, $R^{5AC}$, $R^{5AD}$, and $R^{5AE}$ is, independently, selected from H, $C_{1-4}$ alkyl, $C_{2-4}$ alkenyl, $C_{2-4}$ alkynyl, and $C_{2-4}$ heteroalkyl; each of $R^{5D}$, $R^{5E}$, $R^{5F}$, and $R^{5G}$ is, independently, selected from H, $C_{1-4}$ alkyl, $C_{2-4}$ alkenyl, $C_{2-4}$ alkynyl, $C_{2-4}$ heteroalkyl, $C_{2-6}$ heterocyclyl, $C_{6-12}$ aryl, $C_{7-14}$ alkaryl, and $C_{3-10}$ alkheterocyclyl; $R^{5H}$ is H or $C_{1-4}$ alkyl; and each of $R^{5J}$, $R^{5K}$, and $R^{5L}$ is, independently, selected from H, $C_{1-4}$ alkyl, $C_{2-4}$ alkenyl, $C_{2-4}$ alkynyl, and $C_{2-4}$ heteroalkyl; or $R^{5J}$ and $R^{5K}$ together complete a heterocyclic ring having two nitrogen atoms. Where $R^{5J}$ and $R^{5K}$ form a heterocyclic ring having two nitrogen atoms, the resulting guanidine group is, desirably, selected from

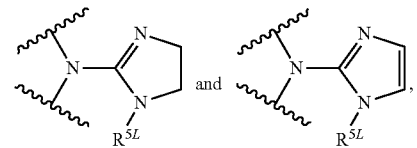

where $R^{5L}$ is H or $CH_3$. Desirably, $R^{5J}$ and $R^{5K}$ combine to form an alkylene or alkenylene of from 2 to 4 carbon atoms, e.g., ring systems of 5, 6, and 7-membered rings. The guanylated nitrogen in formula V is identified herein as N'. Exemplary compounds of formula V include N-guanidyl derivatives (e.g., —C(NH)NH$_2$ derivatives) of anesthetic drugs, such as such as desethyl-N'-guanidyl procaine, desethyl-N'-guanidyl proparacaine, desethyl-N'-guanidyl allocain, desmethyl-N'-guanidyl encainide, desethyl-N'-guanidyl procainamide, desethyl-N'-guanidyl metoclopramide, desmethyl-N'-guanidyl stovaine, desethyl-N'-guanidyl propoxycaine, desethyl-N'-guanidyl chloroprocaine, N'-guanidyl flecainide, and desethyl-N'-guanidyl tetracaine. These derivatives can be prepared using methods analogous to those described in Schemes 2-5.

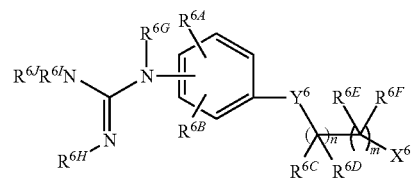

(VI)

In formula VI, n=0-3 and m=0-3, with (n+m)=0-6; each of $R^{6A}$ and $R^{6B}$ is, independently, selected from H, halogen, $C_{1-4}$ alkyl, $C_{2-4}$ alkenyl, $C_{2-4}$ alkynyl, $C_{2-4}$ heteroalkyl, $OR^{6K}$, $NR^{6L}R^{6M}$, $NR^{6N}C(O)R^{6O}$, $S(O)R^{6P}$, $SO_2R^{6Q}R^{6R}$, $SO_2NR^{6S}R^{6T}$, $SO_3R^{6U}$, $CO_2R^{6V}$, $C(O)R^{6W}$, and $C(O)NR^{6X}R^{6Y}$; and each of $R^{6K}$, $R^{6L}$, $R^{6M}$, $R^{6N}$, $R^{6O}$, $R^{6P}$, $R^{6Q}$, $R^{6R}$, $R^{6S}$, $R^{6T}$, $R^{6U}$, $R^{6V}$, $R^{6W}$, $R^{6X}$, and $R^{6Y}$ is, independently, selected from H, $C_{1-4}$ alkyl, $C_{2-4}$ alkenyl, $C_{2-4}$ alkynyl, and $C_{2-4}$ heteroalkyl; $Y^6$ is selected from —CR$^{6Z}$R$^{6AA}$—, NR$^{6AB}$C(O)—, —OC(O)—, —SC(O)—, —C(O)NR$^{6AC}$—, —CO$_2$—, and —OC(S)—; and each of R$^{6Z}$, R$^{6AA}$, R$^{6AB}$, and R$^{6AC}$ is, independently, selected from H, C$_{1-4}$ alkyl, C$_{2-4}$ alkenyl, C$_{2-4}$ alkynyl, and C$_{2-4}$ heteroalkyl; each of R$^{6C}$, R$^{6D}$, R$^{6E}$ and R$^{6F}$ is, independently, selected from H, C$_{1-4}$ alkyl, C$_{2-4}$ alkenyl, C$_{2-4}$ alkynyl, C$_{2-4}$ heteroalkyl, C$_{2-6}$ heterocyclyl, C$_{6-12}$ aryl, C$_{7-14}$ alkaryl, and C$_{3-10}$ alkheterocyclyl; X$^6$ is selected from H, C$_{1-4}$ alkyl, C$_{2-4}$ alkenyl, C$_{2-4}$ alkynyl, and NR$^{6AD}$R$^{6AE}$; each of R$^{6AD}$ and R$^{6AE}$ is, independently, selected from H, C$_{1-4}$ alkyl, C$_{2-4}$ alkenyl, C$_{2-4}$ alkynyl, and C$_{2-4}$ heteroalkyl; R$^{6G}$ is H or C$_{1-4}$ alkyl; and each of R$^{6H}$, R$^{6I}$, and R$^{6J}$ is, independently, selected from H, C$_{1-4}$ alkyl, C$_{2-4}$ alkenyl, C$_{2-4}$ alkynyl, and C$_{2-4}$ heteroalkyl; or R$^{6H}$ and R$^{6I}$ together complete a heterocyclic ring having two nitrogen atoms. Where R$^{6H}$ and R$^{6I}$ form a heterocyclic ring having two nitrogen atoms, the resulting guanidine group is desirably selected from

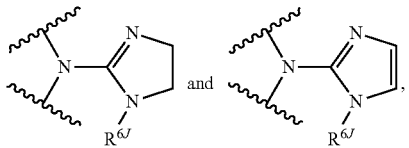

where R$^{6J}$ is H or CH$_3$. Desirably, R$^{6H}$ and R$^{6I}$ combine to form an alkylene or alkenylene of from 2 to 4 carbon atoms, e.g., ring systems of 5, 6, and 7-membered rings. The guanylated nitrogen in formula V is identified herein as N". Exemplary compounds of formula VI include N-guanidyl derivatives (e.g., —C(NH)NH$_2$ derivatives) of anesthetic drugs, such as such as N"-guanidyl procaine, N"-guanidyl proparacaine, N"-guanidyl procainamide, N"-guanidyl metoclopramide, N"-guanidyl propoxycaine, N"-guanidyl chloroprocaine, N"-guanidyl tetracaine, N"-guanidyl benzocaine, and N"-guanidyl butamben. These derivatives can be prepared using methods analogous to those described in Schemes 2-5.

The synthesis of parent drugs of formulas III-VI are described in the literature. See, for example, U.S. Pat. No. 812,554 (synthesis of procaine), Clinton et al., *J. Am. Chem. Soc.* 74:592 (1952) (synthesis of proparacaine), U.S. Pat. No. 2,689,248 (synthesis of propoxycaine), Hadicke et al, *Pharm. Zentralh.* 94:384 (1955) (synthesis of chloroprocaine), U.S. Pat. No. 1,889,645 (synthesis of tetracaine), Salkowski et al., *Ber.* 28:1921 (1895) (synthesis of benzocaine), Brill et al., *J. Am. Chem. Soc.* 43:1322 (1921) (synthesis of butamben), U.S. Pat. No. 3,931,195 (synthesis of encainide), Yamazaki et al., *J. Pharm. Soc. Japan* 73:294 (1953) (synthesis of procainamide), U.S. Pat. No. 3,177,252 (synthesis of metoclopramide), U.S. Pat. No. 3,900,481 (synthesis of flecainide), and Fourneau et al., *Bull. Sci. Pharmacol.* 35:273 (1928) (synthesis of stovaine).

(VII)

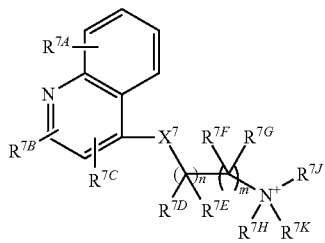

In formula VII, n=0-3 and m=0-3, with (n+m)=0-6; each of R$^{7A}$, R$^{7B}$, and R$^{7C}$ is, independently, selected from H, halogen, C$_{1-4}$ alkyl, C$_{2-4}$ alkenyl, C$_{2-4}$ alkynyl, C$_{2-4}$ heteroalkyl, OR$^{7L}$, NR$^{7M}$R$^{7N}$, NR$^{7O}$C(O)R$^{7P}$, S(O)R$^{7Q}$, SO$_2$R$^{7R}$R$^{7S}$, SO$_2$NR$^{7T}$R$^{7U}$, SO$_3$R$^{7V}$, CO$_2$R$^{7W}$, C(O)R$^{7X}$, and C(O)NR$^{7Y}$R$^{7Z}$; and each of R$^{7L}$, R$^{7M}$, R$^{7N}$, R$^{7O}$, R$^{7P}$, R$^{7Q}$, R$^{7R}$, R$^{7S}$, R$^{7T}$, R$^{7U}$, R$^{7V}$, R$^{7W}$, R$^{7X}$, R$^{7Y}$, and R$^{7Z}$ is, independently, selected from H, C$_{1-4}$ alkyl, C$_{2-4}$ alkenyl, C$_{2-4}$ alkynyl, and C$_{2-4}$ heteroalkyl; X$^7$ is selected from —CR$^{7AA}$R$^{7AB}$—, —NR$^{7AC}$C(O)—, —OC(O)—, —SC(O)—, —C(O)NR$^{7AD}$—, —CO$_2$—, and —OC(S)—; and each of R$^{7AA}$, R$^{7AB}$, R$^{7AC}$, and R$^{7AD}$ is, independently, selected from H, C$_{1-4}$ alkyl, C$_{2-4}$ alkenyl, C$_{2-4}$ alkynyl, and C$_{2-4}$ heteroalkyl; each of R$^{7D}$, R$^{7E}$, R$^{7F}$, and R$^{7G}$ is, independently, selected from H, C$_{1-4}$ alkyl, C$_{2-4}$ alkenyl, C$_{2-4}$ alkynyl, C$_{2-4}$ heteroalkyl, C$_{2-6}$ heterocyclyl, C$_{6-12}$ aryl, C$_{7-14}$ alkaryl, and C$_{3-10}$ alkheterocyclyl; and each of R$^{7H}$, R$^{7J}$, and R$^{7K}$ is, independently, selected from C$_{1-4}$ alkyl, C$_{2-4}$ alkenyl, C$_{2-4}$ alkynyl, and C$_{2-4}$ heteroalkyl. In a preferred embodiment, X$^7$ is —C(O)NH—. Exemplary compounds of formula VII include methylated quaternary ammonium derivatives of anesthetic drugs, such as N'-methyl dibucaine. These derivatives can be prepared using methods analogous to those described in Scheme 1.

(VIII)

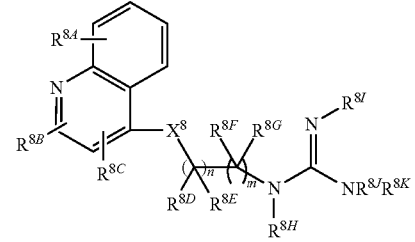

In formula VIII, n=0-3 and m=0-3, with (n+m)=0-6; each of R$^{8A}$, R$^{8B}$, and R$^{8C}$ is, independently, selected from H, halogen, C$_{1-4}$ alkyl, C$_{2-4}$ alkenyl, C$_{2-4}$ alkynyl, C$_{2-4}$ heteroalkyl, OR$^{8L}$, NR$^{8M}$R$^{8N}$, NR$^{8O}$C(O)R$^{8P}$, S(O)R$^{8Q}$, SO$_2$R$^{8R}$R$^{8S}$, SO$_2$NR$^{8T}$R$^{8U}$, SO$_3$R$^{8V}$, CO$_2$R$^{8W}$, C(O)R$^{8X}$, and C(O)NR$^{8Y}$R$^{8Z}$; and each of R$^{8L}$, R$^{8M}$, R$^{8N}$, R$^{8O}$, R$^{8P}$, R$^{8Q}$, R$^{8R}$, R$^{8S}$, R$^{8T}$, R$^{8U}$, R$^{8V}$, R$^{8W}$, R$^{8X}$, R$^{8Y}$, and R$^{8Z}$ is, independently, selected from H, C$_{1-4}$ alkyl, C$_{2-4}$ alkenyl, C$_{2-4}$ alkynyl, and C$_{2-4}$ heteroalkyl; X$^8$ is selected from —CR$^{8AA}$R$^{8AB}$—, —NR$^{8AC}$C(O)—, —OC(O)—, —SC(O)—, —C(O)NR$^{8AD}$—, —CO$_2$—, and —OC(S)—; and each of R$^{8AA}$, R$^{8AB}$, R$^{8AC}$, and R$^{8AD}$ is, independently, selected from H, C$_{1-4}$ alkyl, C$_{2-4}$ alkenyl, C$_{2-4}$ alkynyl, and C$_{2-4}$ heteroalkyl; each of R$^{8D}$, R$^{8E}$, R$^{8F}$, and R$^{8G}$ is, independently, selected from H, C$_{1-4}$ alkyl, C$_{2-4}$ alkenyl, C$_{2-4}$ alkynyl, C$_{2-4}$ heteroalkyl, C$_{2-6}$ heterocyclyl, C$_{6-12}$ aryl, C$_{7-14}$ alkaryl, and C$_{3-10}$ alkheterocyclyl; R$^{8H}$ is H or C$_{1-4}$ alkyl; and each of R$^{8I}$, R$^{8J}$, and R$^{8K}$ is, independently, selected from H, C$_{1-4}$ alkyl, C$_{2-4}$ alkenyl, C$_{2-4}$ alkynyl, and C$_{2-4}$ heteroalkyl; or R$^{8I}$ and R$^{8J}$ together complete a heterocyclic ring having two nitrogen atoms. Where R$^{8I}$ and R$^{8J}$ form a heterocyclic ring having two nitrogen atoms, the resulting guanidine group is, desirably, selected from where $R^{8K}$ is H or $CH_3$. Desirably, $R^{8I}$ and $R^{8J}$ combine to form an alkylene or alkenylene of from 2 to 4 carbon atoms, e.g., ring systems of 5, 6, and 7-membered rings. The guanylated nitrogen in formula V is identified herein as N'. In a preferred embodiment, $X^8$ is —C(O)NH—. Exemplary compounds of formula VIII include N-guanidyl derivatives (e.g., —C(NH)NH$_2$ derivatives) of anesthetic drugs, such as such as desethyl-N-guanidyl dibucaine. These derivatives can be prepared using methods analogous to those described in Schemes 2-5.

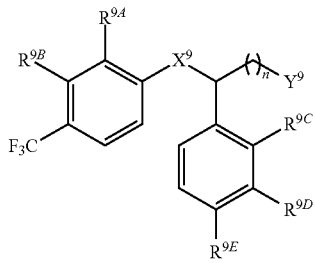

(IX)

In formula IX, n=0-6; each of $R^{9A}$, $R^{9B}$, $R^{9C}$, $R^{9D}$, and $R^{9F}$ is, independently, selected from H, halogen, $C_{1-4}$ alkyl, $C_{2-4}$ alkenyl, $C_{2-4}$ alkynyl, $OR^{9I}$, $NR^{9J}R^{9K}$, $NR^{9L}C(O)R^{9M}$, $S(O)R^{9N}$, $SO_2R^{9O}R^{9P}$, $SO_2NR^{9Q}R^{9R}$, $SO_3R^{9S}$, $CO_2R^{9T}$, $C(O)R^{9U}$, and $C(O)NR^{9V}R^{9W}$; and each of $R^{9I}$, $R^{9J}$, $R^{9K}$, $R^{9L}$, $R^{9M}$, $R^{9N}$, $R^{9O}$, $R^{9P}$, $R^{9Q}$, $R^{9R}$, $R^{9S}$, $R^{9T}$, $R^{9U}$, $R^{9V}$, and $R^{9W}$ is, independently, selected from H, $C_{1-4}$ alkyl, $C_{2-4}$ alkenyl, $C_{2-4}$ alkynyl, and $C_{2-4}$ heteroalkyl; $X^9$ is selected from —$CR^{9X}R^{9Y}$—, —O—, —S—, and —$NR^{9Z}$—; and each of $R^{9X}$, $R^{9Y}$, and $R^{9Z}$ is, independently, selected from H, $C_{1-4}$ alkyl, $C_{2-4}$ alkenyl, $C_{2-4}$ alkynyl, and $C_{2-4}$ heteroalkyl; $Y^9$ is $NR^{9AA}R^{9AB}R^{9AC}$ or $NR^{9AD}Z^9$; each of $R^{9AA}$, $R^{9AB}$, and $R^{9AC}$ is, independently, selected from H, $C_{1-4}$ alkyl, $C_{2-4}$ alkenyl, and $C_{2-4}$ alkynyl; $R^{9AD}$ is H or $C_{1-4}$ alkyl; $Z^9$ is

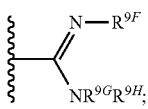

and
each of $R^{9F}$, $R^{9G}$, and $R^{9H}$ is, independently, selected from H, $C_{1-4}$ alkyl, $C_{2-4}$ alkenyl, and $C_{2-4}$ alkynyl, or $R^{9F}$ and $R^{9G}$ together complete a heterocyclic ring having two nitrogen atoms. Where $R^{9F}$ and $R^{9G}$ form a heterocyclic ring having two nitrogen atoms, the resulting guanidine group is, desirably, selected from

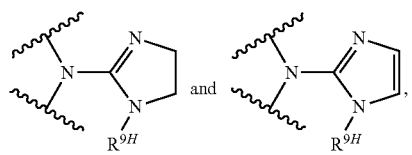

where $R^{9H}$ is H or $CH_3$. Desirably, $R^{9F}$ and $R^{9G}$ combine to form an alkylene or alkenylene of from 2 to 4 carbon atoms, e.g., ring systems of 5, 6, and 7-membered rings. In a preferred embodiment, $X^9$=—O—. Exemplary compounds of formula IX include N-guanidyl derivatives (e.g., —C(NH)NH$_2$ derivatives), such as N-guanidyl fluoxetine, and methylated quaternary ammonium derivatives, such as N,N-dimethyl fluoxetine. These derivatives can be prepared using methods analogous to those described in Schemes 1-5.

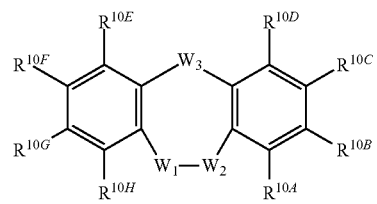

(X)

In formula X, $W_3$ is O, NH, $NCH_2R^{10J}$, $NC(O)CH_2R^{10J}$, $CHCH_2R^{10J}$, C=$CHR^{10J}$, or C=$CHR^{10K}$; $W_1$-$W_2$ is S, O, $OCHR^{10K}$, $SCHR^{10K}$, N=$CR^{10K}$, $CHR^{10K}$, $CHR^{10L}$—$CHR^{10K}$, or $CR^{10L}$=$CR^{10L}$; each of $R^{10A}$, $R^{10B}$, $R^{10C}$, $R^{10D}$, $R^{10E}$, $R^{10F}$, $R^{10G}$, and $R^{10H}$ is, independently, selected from H, OH, halide, $C_{1-4}$ alkyl, and $C_{2-4}$ heteroalkyl; $R^{10J}$ is $CH_2CH_2X^{10A}$ or $CH(CH_3)CH_2X^{10A}$; $R^{10L}$ is H or OH; $R^{10K}$ is H, OH, or the group:

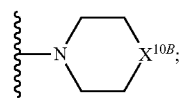

$X^{10A}$ is $NR^{10M}R^{10N}R^{10P}$, or $NR^{10Q}X^{10C}$; $X^{10B}$ is $NR^{10R}R^{10S}$, or $NX^{10C}$; each of $R^{10M}$, $R^{10N}$, $R^{10P}$, $R^{10R}$, and $R^{10S}$ is, independently, selected from $C_{1-4}$ alkyl, $C_{2-4}$ alkenyl, $C_{2-4}$ alkynyl, and $C_{2-4}$ heteroalkyl, or $R^{10R}$ and $R^{10S}$ together complete a heterocyclic ring having at least one nitrogen atom; $R^{10Q}$ is H or $C_{1-4}$ alkyl; $X^{10C}$ is

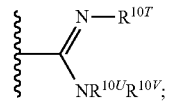

and
each of $R^{10T}$, $R^{10U}$, and $R^{10V}$ is, independently, selected from H, $C_{1-4}$ alkyl, $C_{2-4}$ alkenyl, and $C_{2-4}$ alkynyl, or $R^{10T}$ and $R^{10V}$ together complete a heterocyclic ring having two nitrogen atoms. Where $R^{10T}$ and $R^{10V}$ form a heterocyclic ring having two nitrogen atoms, the resulting guanidine group is, desirably, selected from

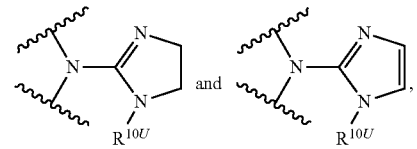

where $R^{10U}$ is H or $CH_3$. Desirably, $R^{10T}$ and $R^{10V}$ combine to form an alkylene or alkenylene of from 2 to 4 carbon atoms, e.g., ring systems of 5, 6, and 7-membered rings. Exemplary compounds of formula X include N-guanidyl derivatives (e.g., —C(NH)NH$_2$ derivatives) and methylated quaternary ammonium derivatives. N-guanidyl derivatives of formula X include, without limitation, N-guanidyl amoxapine, desmethyl-N-guanidyl trimipramine, desmethyl-N- guanidyl dothiepin, desmethyl-N-guanidyl doxepin, desmethyl-N-guanidyl amitriptyline, N-guanidyl protriptyline, N-guanidyl desipramine, desmethyl-N-guanidyl clomipramine, desmethyl-N-guanidyl clozapine, desmethyl-N-guanidyl loxapine, N-guanidyl nortriptyline, desmethyl-N-guanidyl cyclobenzaprine, desmethyl-N-guanidyl cyproheptadine, desmethyl-N-guanidyl olopatadine, desmethyl-N-guanidyl promethazine, desmethyl-N-guanidyl trimeprazine, desmethyl-N-guanidyl chlorprothixene, desmethyl-N-guanidyl chlorpromazine, desmethyl-N-guanidyl propiomazine, desmethyl-N-guanidyl prochlorperazine, desmethyl-N-guanidyl thiethylperazine, desmethyl-N-guanidyl trifluoperazine, desethyl-N-guanidyl ethacizine, and desmethyl-N-guanidyl imipramine. Methylated quaternary ammonium derivatives of formula X include, without limitation, N,N-dimethyl amoxapine, N-methyl trimipramine, N-methyl dothiepin, N-methyl doxepin, N-methyl amitriptyline, N,N-dimethyl protriptyline, N,N-dimethyl desipramine, N-methyl clomipramine, N-methyl clozapine, N-methyl loxapine, N,N-dimethyl nortriptyline, N-methyl cyclobenzaprine, N-methyl cyproheptadine, N-methyl olopatadine, N-methyl promethazine, N-methyl trimeprazine, N-methyl chlorprothixene, N-methyl chlorpromazine, N-methyl propiomazine, N-methyl moricizine, N-methyl prochlorperazine, N-methyl thiethylperazine, N-methyl fluphenazine, N-methyl perphenazine, N-methyl flupenthixol, N-methyl acetophenazine, N-methyl trifluoperazine, N-methyl ethacizine, and N-methyl imipramine. These derivatives can be prepared using methods analogous to those described in Schemes 1-5.

Other ion channel blockers that can contain an amine nitrogen which can be guanylated or quaternized as described herein include, without limitation, orphenadrine, phenbenzamine, bepridil, pimozide, penfluridol, flunarizine, fluspirilene, propiverine, disopyramide, methadone, tolterodine, tridihexethyl salts, tripelennamine, mepyramine, brompheniramine, chlorpheniramine, dexchlorpheniramine, carbinoxamine, levomethadyl acetate, gallopamil, verapamil, devapamil, tiapamil, emopamil, dyclonine, pramoxine, lamotrigine, mibefradil, gabapentin, amiloride, diltiazem, nifedipine, nimodipine, nitrendipine, cocaine, mexiletine, propafenone, quinidine, oxethazaine, articaine, riluzole, bencyclane, lifarizine, and strychnine. Still other ion channel blockers can be modified to incorporate a nitrogen atom suitable for quaternization or guanylation. These ion channel blockers include, without limitation, fosphenytoin, ethotoin, phenytoin, carbamazepine, oxcarbazepine, topiramate, zonisamide, and salts of valproic acid.

Synthesis

The synthesis of charge-modified ion channel blockers may involve the selective protection and deprotection of alcohols, amines, ketones, sulfhydryls or carboxyl functional groups of the parent ion channel blocker, the linker, the bulky group, and/or the charged group. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxyls include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxyl functionalities and the conditions required for their removal are provided in detail in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994.

Charge-modified ion channel blockers can be prepared using techniques familiar to those skilled in the art. The modifications can be made, for example, by alkylation of the parent ion channel blocker using the techniques described by J. March, Advanced Organic Chemistry: Reactions, Mechanisms and Structure, John Wiley & Sons, Inc., 1992, page 617. The conversion of amino groups to guanidine groups can be accomplished using standard synthetic protocols. For example, Mosher has described a general method for preparing mono-substituted guanidines by reaction of aminoiminomethanesulfonic acid with amines (Kim et al., *Tetrahedron Lett.* 29:3183 (1988)). A more convenient method for guanylation of primary and secondary amines was developed by Bernatowicz employing 1H-pyrazole-1-carboxamidine hydrochloride; 1-H-pyrazole-1-(N,N'-bis(tert-butoxycarbonyl)carboxamidine; or 1-H-pyrazole-1-(N,N'-bis(benzyloxycarbonyl)carboxamidine. These reagents react with amines to give mono-substituted guanidines (see Bernatowicz et al., *J. Org. Chem.* 57:2497 (1992); and Bernatowicz et al., *Tetrahedron Lett.* 34:3389 (1993)). In addition, Thioureas and S-alkyl-isothioureas have been shown to be useful intermediates in the syntheses of substituted guanidines (Poss et al., *Tetrahedron Lett.* 33:5933 (1992)). In certain embodiments, the guanidine is part of a heterocyclic ring having two nitrogen atoms (see, for example, the structures below). The ring system can include an alkylene or

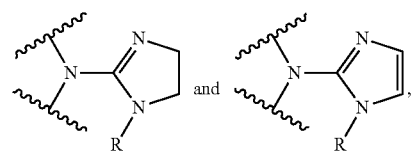

alkenylene of from 2 to 4 carbon atoms, e.g., ring systems of 5, 6, and 7-membered rings. Such ring systems can be prepared, for example, using the methods disclosed by Schlama et al., *J. Org. Chem.*, 62:4200 (1997).

Charge-modified ion channel blockers can be prepared by alkylation of an amine nitrogen in the parent compound as shown in Scheme 1.

Scheme 1

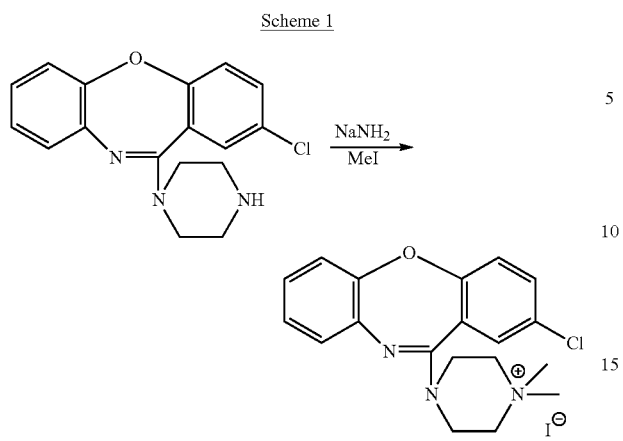

Alternatively, charge-modified ion channel blockers can be prepared by introduction of a guanidine group. The parent compound can be reacted with a cynamide, e.g., methylcyanamide, as shown in Scheme 2 or pyrazole-1-carboxamidine derivatives as shown in Scheme 3 where Z is H or a suitable protecting group. Alternatively, the parent compound can be reacted with cyanogens bromide followed by reaction with methylchloroaluminum amide as shown in Scheme 4. Reagents such as 2-(methylthio)-2-imidazoline can also be used to prepare suitably functionalized derivatives (Scheme 5).

Scheme 2

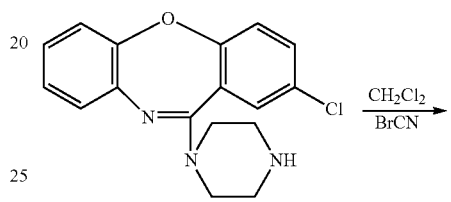

Scheme 3

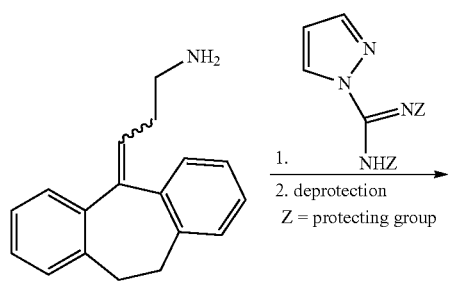

Scheme 4

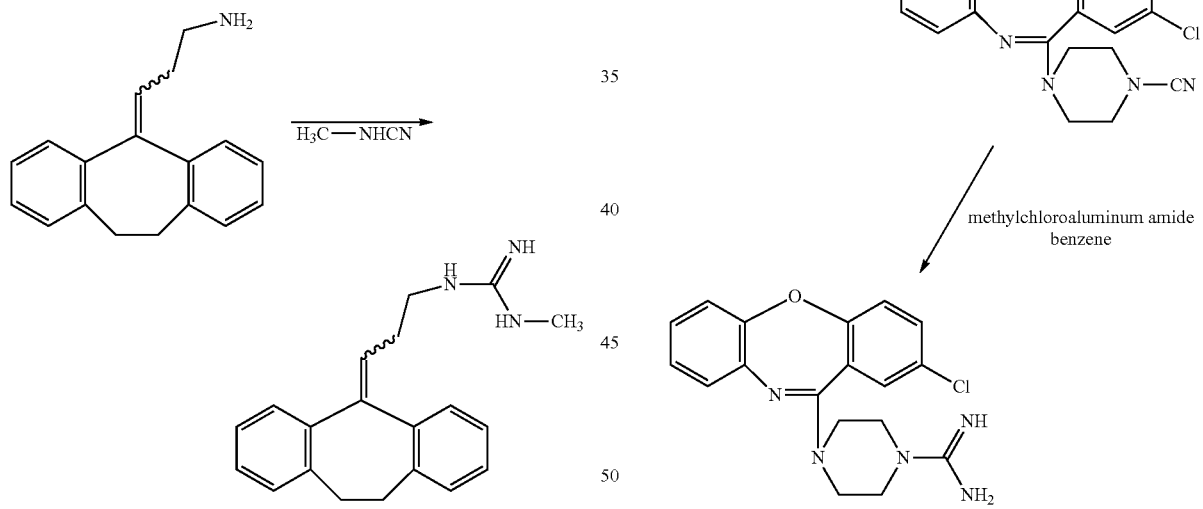

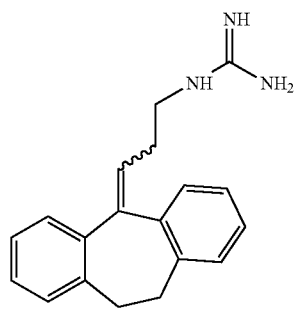

Scheme 5

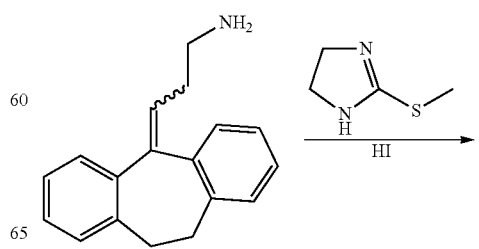

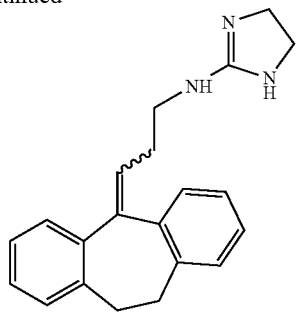

Any ion channel blocker containing an amine nitrogen atom can be modified as shown in Schemes 1-5.

TRPV1 Agonists

TRPV1 agonists that can be employed in the methods, compositions, and kits of the invention include but are not limited to any that activates TRPV1 receptors on nociceptors and allows for entry of at least one inhibitor of voltage-gated ion channels. Suitable TRPV1 agonists include but are not limited to capsaicin, eugenol, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), C18 N-acylethanolamines, lipoxygenase derivatives such as 12-hyperoxyeicosatetraenoic acid, inhibitor cysteine knot (ICK) peptides (vanillotoxins), piperine, MSK195 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-alpha-sanshool, 2-aminoethoxydiphenyl borate, 10-shogaol, oleylgingerol, oleylshogaol, and SU200 (N-(4-tert-butylbenzyl)-N'-(4-hydroxy-3-methoxybenzyl)thiourea).

TRP1A Agonists

TRP1A agonists that can be employed in the methods, compositions, and kits of the invention include any that activates TRP1A receptors on nociceptors or pruriceptors and allows for entry of at least one inhibitor of voltage-gated ion channels. Suitable TRP1A agonists include but are not limited to cinnamaldehyde, allyl-isothiocynanate, diallyl disulfide, icilin, cinnamon oil, wintergreen oil, clove oil, acrolein, hydroxy-alpha-sanshool, 2-aminoethoxydiphenyl borate, 4-hydroxynonenal, methyl p-hydroxybenzoate, mustard oil, and 3'-carbamoylbiphenyl-3-yl cyclohexylcarbamate (URB597).

P2X Agonists

P2X agonists that can be employed in the methods, compositions, and kits of the invention include any that activates P2X receptors on nociceptors or pruriceptors and allows for entry of at least one inhibitor of voltage-gated ion channels. Suitable P2X agonists include but are not limited to 2-methylthio-ATP, 2' and 3'-O-(4-benzoylbenzoyl)-ATP, and ATP5'-O-(3-thiotriphosphate).

TRPM8 Agonists

TRPM8 agonists that can be employed in the methods, compositions, and kits of the invention include any that activates TRPM8 receptors on nociceptors or pruriceptors and allows for entry of at least one inhibitor of voltage-gated ion channels. Suitable TRPM8 agonists include but are not limited to menthol, iciclin, eucalyptol, linalool, geraniol, and hydroxycitronellal.

Additional Agents

The methods, compositions, and kits of the invention may be used for the treatment of pain (e.g., neuropathic pain, nociceptive pain, idiopathic pain, inflammatory pain, dysfunctional pain, migraine, or procedural pain) and itch (e.g. dermatological conditions like atopic eczema or psoriasis, pruritis in parasitic and fungal infections, drug-induced, allergic, metabolic, in cancer or liver and kidney failure). If desired, one or more additional agents typically used to treat pain may be used in conjunction with a combination of the invention in the methods, compositions, and kits described herein. Such agents include but are not limited to NSAIDs, opioids, tricyclic antidepressants, amine transporter inhibitors, anticonvulsants. If desired, one or more additional agents typically used to treat itch may be used in conjunction with a combination of the invention in the methods, compositions, and kits described herein. Such agents include topical or oral steroids and antihistamines.

Formulation of Compositions

The administration of a combination of the invention may be by any suitable means that results in the reduction of pain sensation at the target region. The inhibitor(s) of voltage-gated ion channels and the TRPV1/TRPA1/P2X/TRPM8 receptor agonist(s) may be contained in any appropriate amount in any suitable carrier substance, and are generally present in amounts totaling 1-95% by weight of the total weight of the composition. The composition may be provided in a dosage form that is suitable for oral, parenteral (e.g., intravenous, intramuscular), rectal, cutaneous, subcutaneous, topical, transdermal, sublingual, nasal, vaginal, intrathecal, epidural, or ocular administration, or by injection, inhalation, or direct contact with the nasal or oral mucosa.

Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Each compound of the combination may be formulated in a variety of ways that are known in the art. For example, the first and second agents may be formulated together or separately. Desirably, the first and second agents are formulated together for the simultaneous or near simultaneous administration of the agents.

The individually or separately formulated agents can be packaged together as a kit. Non-limiting examples include but are not limited to kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions.

The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary. It may be useful to administer the minimum therapeutic dose required to activate the TRPV1/TRPA1/P2X/TRPM8 receptor, which can be determined using standard techniques.

Administration of each drug in the combination can, independently, be one to four times daily for one day to one year, and may even be for the life of the patient. Chronic, long-term administration will be indicated in many cases.

Topical Formulations

Compositions can also be adapted for topical use with a topical vehicle containing from between 0.0001% and 25% (w/w) or more of active ingredient(s).

In a preferred combination, the active ingredients are preferably each from between 0.0001% to 10% (w/w), more preferably from between 0.0005% to 4% (w/w) active agent. The cream can be applied one to four times daily, or as needed. For example, for prednisolone adapted for topical administration, a topical vehicle will contain from between 0.01% to 5% (w/w), preferably from between 0.01% to 2% (w/w), more preferably from between 0.01% to 1% (w/w).

Performing the methods described herein, the topical vehicle containing the combination of the invention is preferably applied to the site of discomfort on the subject. For example, a cream may be applied to the hands of a subject suffering from arthritic fingers.

Conjugates

If desired, the drugs used in any of the combinations described herein may be covalently attached to one another to form a conjugate of formula (XI).

(A)-(L)-(B)   (XI)

In formula (XI), (A) is a compound that activates a channel-forming receptor that is present on nociceptors and/or pruriceptors; (L) is a linker; and (B) is a compound that inhibits one or more voltage-gated ion channels when applied to the internal face of the channels but does not substantially inhibit the channels when applied to the external face of the channels, and is capable of entering nociceptors or pruriceptors through the channel-forming receptor when the receptor is activated.

The conjugates of the invention can be prodrugs, releasing drug (A) and drug (B) upon, for example, cleavage of the conjugate by intracellular and extracellular enzymes (e.g., amidases, esterases, and phosphatases). The conjugates of the invention can also be designed to largely remain intact in vivo, resisting cleavage by intracellular and extracellular enzymes, so long as the conjugate and is capable of entering nociceptors or pruriceptors through the channel-forming receptor when the receptor is activated. The degradation of the conjugate in vivo can be controlled by the design of linker (L) and the covalent bonds formed with compound (A) and compound (B) during the synthesis of the conjugate.

Conjugates can be prepared using techniques familiar to those skilled in the art. For example, the conjugates can be prepared using the methods disclosed in G. Hermanson, Bioconjugate Techniques, Academic Press, Inc., 1996. The synthesis of conjugates may involve the selective protection and deprotection of alcohols, amines, ketones, sulfhydryls or carboxyl functional groups of drug (A), the linker, and/or drug (B). For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxyls include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxyl functionalities and the conditions required for their removal are provided in detail in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994. Additional synthetic details are provided below.

Linkers

The linker component of the invention is, at its simplest, a bond between compound (A) and compound (B), but typically provides a linear, cyclic, or branched molecular skeleton having pendant groups covalently linking compound (A) to compound (B). Thus, linking of compound (A) to compound (B) is achieved by covalent means, involving bond formation with one or more functional groups located on compound (A) and compound (B). Examples of chemically reactive functional groups which may be employed for this purpose include, without limitation, amino, hydroxyl, sulfhydryl, carboxyl, carbonyl, carbohydrate groups, vicinal diols, thioethers, 2-aminoalcohols, 2-aminothiols, guanidinyl, imidazolyl, and phenolic groups.

The covalent linking of compound (A) and compound (B) may be effected using a linker which contains reactive moieties capable of reaction with such functional groups present in compound (A) and compound (B). For example, an amine group of compound (A) may react with a carboxyl group of the linker, or an activated derivative thereof, resulting in the formation of an amide linking the two.

Examples of moieties capable of reaction with sulfhydryl groups include α-haloacetyl compounds of the type $XCH_2CO-$ (where X=Br, Cl or I), which show particular reactivity for sulfhydryl groups, but which can also be used to modify imidazolyl, thioether, phenol, and amino groups as described by Gurd, *Methods Enzymol.* 11:532 (1967). N-Maleimide derivatives are also considered selective towards sulfhydryl groups, but may additionally be useful in coupling to amino groups under certain conditions. Reagents such as 2-iminothiolane (Traut et al., *Biochemistry* 12:3266 (1973)), which introduce a thiol group through conversion of an amino group, may be considered as sulfhydryl reagents if linking occurs through the formation of disulphide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type $XCH_2CO-$ (where X=Cl, Br or I), for example, as described by Wong *Biochemistry* 24:5337 (1979);

(ii) N-maleimide derivatives, which may react with amino groups either through a Michael type reaction or through acylation by addition to the ring carbonyl group, for example, as described by Smyth et al., *J. Am. Chem. Soc.* 82:4600 (1960) and *Biochem. J.* 91:589 (1964);

(iii) aryl halides such as reactive nitrohaloaromatic compounds;

(iv) alkyl halides, as described, for example, by McKenzie et al., *J. Protein Chem.* 7:581 (1988);

(v) aldehydes and ketones capable of Schiff's base formation with amino groups, the adducts formed usually being stabilized through reduction to give a stable amine;

(vi) epoxide derivatives such as epichlorohydrin and bisoxiranes, which may react with amino, sulfhydryl, or phenolic hydroxyl groups;

(vii) chlorine-containing derivatives of s-triazines, which are very reactive towards nucleophiles such as amino, sufhydryl, and hydroxyl groups;

(viii) aziridines based on s-triazine compounds detailed above, e.g., as described by Ross, *J. Adv. Cancer Res.* 2:1 (1954), which react with nucleophiles such as amino groups by ring opening;

(ix) squaric acid diethyl esters as described by Tietze, *Chem. Ber.* 124:1215 (1991); and (x) α-haloalkyl ethers, which are more reactive alkylating agents than normal alkyl halides because of the activation caused by the ether oxygen atom, as described by Benneche et al., *Eur. J. Med. Chem.* 28:463 (1993).

Representative amino-reactive acylating agents include:

(i) isocyanates and isothiocyanates, particularly aromatic derivatives, which form stable urea and thiourea derivatives respectively;

(ii) sulfonyl chlorides, which have been described by Herzig et al., *Biopolymers* 2:349 (1964);

(iii) acid halides;

(iv) active esters such as nitrophenylesters or N-hydroxysuccinimidyl esters;

(v) acid anhydrides such as mixed, symmetrical, or N-carboxyanhydrides;

(vi) other useful reagents for amide bond formation, for example, as described by M. Bodansky, Principles of Peptide Synthesis, Springer-Verlag, 1984;

(vii) acylazides, e.g. wherein the azide group is generated from a preformed hydrazide derivative using sodium nitrite, as described by Wetz et al., *Anal. Biochem.* 58:347 (1974); and (viii) imidoesters, which form stable amidines on reaction with amino groups, for example, as described by Hunter and Ludwig, *J. Am. Chem. Soc.* 84:3491 (1962).

Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., in *Bioconjugate Chem.* 1:96 (1990).

Examples of reactive moieties capable of reaction with carboxyl groups include diazo compounds such as diazoacetate esters and diazoacetamides, which react with high specificity to generate ester groups, for example, as described by Herriot, *Adv. Protein Chem.* 3:169 (1947). Carboxyl modifying reagents such as carbodiimides, which react through 0-acylurea formation followed by amide bond formation, may also be employed.

It will be appreciated that functional groups in compound (A) and/or compound (B) may, if desired, be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of compound (A) with a reactive chemical group of compound (B) without introducing additional linking material may, if desired, be used in accordance with the invention.

Most commonly, however, the linker will include two or more reactive moieties, as described above, connected by a spacer element. The presence of such a spacer permits bifunctional linkers to react with specific functional groups within compound (A) and compound (B), resulting in a covalent linkage between the two. The reactive moieties in a linker may be the same (homobifunctional linker) or different (heterobifunctional linker, or, where several dissimilar reactive moieties are present, heteromultifunctional linker), providing a diversity of potential reagents that may bring about covalent attachment between compound (A) and compound (B).

Spacer elements in the linker typically consist of linear or branched chains and may include a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, or $C_{1-10}$ heteroalkyl.

In some instances, the linker is described by formula (XII):

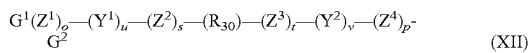
(XII)

In formula (XII), $G^1$ is a bond between compound (A) and the linker; $G^2$ is a bond between the linker and compound (B); $Z^1$, $Z^2$, $Z^3$, and $Z^4$ each, independently, is selected from O, S, and $NR_{31}$; $R_{31}$ is hydrogen, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl; $Y^1$ and $Y^2$ are each, independently, selected from carbonyl, thiocarbonyl, sulphonyl, or phosphoryl; o, p, s, t, u, and v are each, independently, 0 or 1; and $R_{30}$ is a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, or $C_{1-10}$ heteroalkyl, or a chemical bond linking $G^1\text{-}(Z^1)_o\text{---}(Y^1)_u\text{---}(Z^2)_s\text{---}$ to $\text{---}(Z^3)_t\text{---}(Y^2)_v\text{---}(Z^4)_p\text{-}G^2$.

Examples of homobifunctional linkers useful in the preparation of conjugates of the invention include, without limitation, diamines and diols selected from ethylenediamine, propylenediamine and hexamethylenediamine, ethylene glycol, diethylene glycol, propylene glycol, 1,4-butanediol, 1,6-hexanediol, cyclohexanediol, and polycaprolactone diol.

Exemplary Uses

The methods, compositions, and kits of the invention can be used to treat pain associated with any of a number of conditions, including back and neck pain, cancer pain, gynecological and labor pain, fibromyalgia, arthritis and other rheumatological pains, orthopedic pains, post herpetic neuralgia and other neuropathic pains, sickle cell crises, interstitial cystitis, urethritis and other urological pains, dental pain, headaches, postoperative pain, and procedural pain (i.e., pain associated with injections, draining an abcess, surgery, dental procedures, opthalmic procedures, arthroscopies and use of other medical instrumentation, cosmetic surgical procedures, dermatological procedures, setting fractures, biopsies, and the like).

Since a subclass of nociceptors mediate itch sensation the methods, compositions, and kits of the invention can also be used to treat itch in patients with conditions like dermatitis, infections, parasites, insect bites, pregnancy, metabolic disorders, liver or renal failure, drug reactions, allergic reactions, eczema, and cancer.

Pain and Function Indices

In order to measure the efficacy of any of the methods, compositions, or kits of the invention, a measurement index may be used. Indices that are useful in the methods, compositions, and kits of the invention for the measurement of pain associated with musculoskeletal, immunoinflammatory and neuropathic disorders include a visual analog scale (VAS), a Likert scale, categorical pain scales, descriptors, the Lequesne index, the WOMAC index, and the AUSCAN index, each of which is well known in the art. Such indices may be used to measure pain, itch, function, stiffness, or other variables.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain or itch by choosing the spot on the line that best corresponds to the sensation of pain or itch, where one end of the line corresponds to "no pain" (score of 0 cm) or "no itch" and the other end of the line corresponds to "unbearable pain" or "unbearable itch" (score of 10 cm). This procedure provides a simple and rapid approach to obtaining quantitative information about how the patient is experiencing pain or itch. VAS scales and their use are described, e.g., in U.S. Pat. Nos. 6,709,406 and 6,432,937.

A Likert scale similarly provides a measure of a one-dimensional quantity. Generally, a Likert scale has discrete integer values ranging from a low value (e.g., 0, meaning no pain) to a high value (e.g., 7, meaning extreme pain). A patient experiencing pain is asked to choose a number between the low value and the high value to represent the degree of pain experienced Likert scales and their use are described, e.g., in U.S. Pat. Nos. 6,623,040 and 6,766,319.

The Lequesne index and the Western Ontario and McMaster Universities (WOMAC) osteoarthritis index assess pain, function, and stiffness in the knee and hip of OA patients using self-administered questionnaires. Both knee and hip are encompassed by the WOMAC, whereas there is one Lequesne questionnaire for the knee and a separate one for the hip. These questionnaires are useful because they contain more information content in comparison with VAS or Likert. Both the WOMAC index and the Lequesne index questionnaires have been extensively validated in OA, including in surgical settings (e.g., knee and hip arthroplasty). Their metric characteristics do not differ significantly.

The AUSCAN (Australian-Canadian hand arthritis) index employs a valid, reliable, and responsive patient self-reported questionnaire. In one instance, this questionnaire contains 15 questions within three dimensions (Pain, 5 questions; Stiffness, 1 question; and Physical function, 9 questions). An AUSCAN index may utilize, e.g., a Likert or a VAS scale.

Indices that are useful in the methods, compositions, and kits of the invention for the measurement of pain include the Pain Descriptor Scale (PDS), the Visual Analog Scale (VAS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

Itch can be measured by subjective measures (VAS, Lickert, descriptors). Another approach is to measure scratch which is an objective correlate of itch using a vibration transducer or movement-sensitive meters.

Screening

Our discovery that certain channels expressed by and present on nociceptors and pruriceptors allow entry of compounds that inhibit voltage-gated ion channels into the target cells provides a method for identifying compounds as being useful for the treatment of pain and itch. In one example, a nociceptor or pruriceptor is contacted with a one, two, or more compounds that activate TRPV1, TRPA1, TRPM8 and/or P2X(2/3) receptors. The same nociceptor or pruriceptor is also contacted with a second compound that inhibits one or more voltage-gated ion channels when applied to the internal face of the nociceptor (e.g., by intracellular application via micropipette in the whole-cell patch-clamp technique) but not when applied to the external face of the cell (because of the inability of the compound to cross the cell membrane). Inhibition of the ion channels in the nociceptor or pruriceptor will inhibit the cell from propagating an action potential and/or signalling to the second order neuron, in either case blocking the transmission of the pain signal, thus, the ability of the second compound to inhibit voltage-gated ion channels in the nociceptor identifies that compound as one that can be used in combination with compounds that activate TRPV1, TRPA1, TRPM8 and/or P2X(2/3) receptors to treat pain or itch.

The following examples are intended to illustrate the invention, and is not intended to limit it.

Example 1

We recorded current through voltage-dependent sodium channels using whole-cell voltage clamp recordings from adult rat DRG neurons. To select for nociceptors, we recorded from small (24±5 µm; n=25) neurons and tested the neurons for the expression of TRPV1 receptors by a short (1-sec) application of 1 µM capsaicin. In 25/25 of small neurons tested, capsaicin produced a prolonged (10±3 sec) inward current (FIG. 1A, upper panel), consistent with the neurons being nociceptors. Sodium currents were elicited by depolarizing steps from a holding potential of −70 mV. Bath application of 5 mM QX-314 alone had a minimal effect on sodium current (decrease by 3±0.5% after a 5-minute application, n=25) (FIG. 1A, left; b). Application of capsaicin alone (1 µM for 1-10 minutes) reduced sodium current moderately (31±9% inhibition (n=25). However, when QX-314 was applied together with capsaicin, sodium current was nearly totally abolished (inhibition by 98±0.4%, n=25) (FIG. 1A, left; b). As expected if the block of sodium current resulted from gradual entry of QX-314 through TRPV1 receptors, inhibition developed over several minutes and was nearly complete after 15 minutes (FIG. 1C).

To test whether the ability of co-applied capsaicin and QX-314 to inhibit sodium current is selective for cells that express TRPV1 receptors, we also recorded from large DRG neurons (soma diameter >40 µm) (FIG. 1A, right). In these neurons, capsaicin did not elicit an inward current (10 of 10). As for small diameter neurons, QX-314 applied alone had little or no effect on sodium current (current increased by 8±4% after a 10-minute application, n=10). Unlike small diameter neurons, capsaicin had no effect on sodium current in large diameter neurons (average increase by 3±2% after a 10-minute application, n=10). Most notably, co-application of QX-314 and capsaicin had little or no effect on sodium current in the large diameter neurons (decrease by 9±5% after a 10-minute application, n=10). Thus, the ability of co-applied QX-314 and capsaicin to inhibit sodium current is highly selective for neurons expressing TRPV1 receptors, as expected if QX-314 enters the neurons through TRPV1 receptors.

Figure 2B:
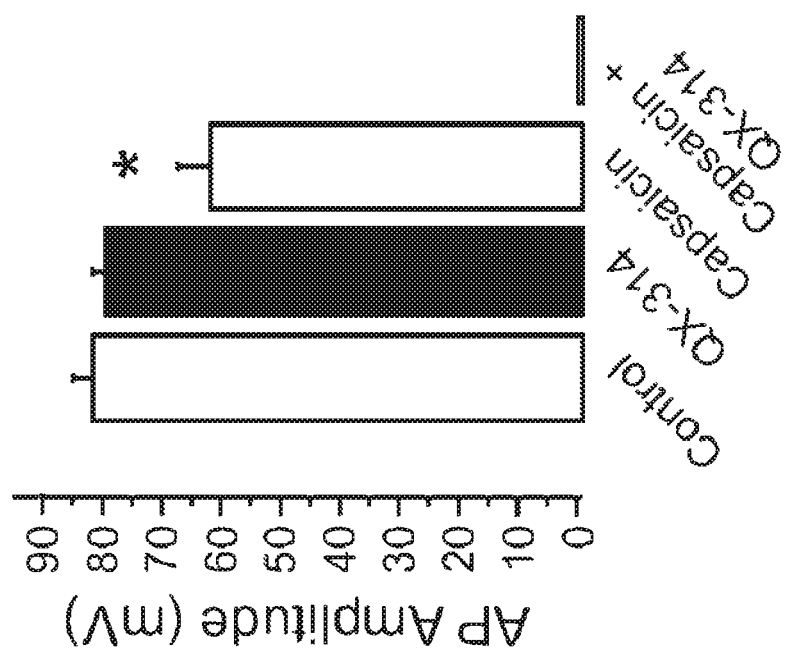

We also examined the effect of co-applied QX-314 and capsaicin in current clamp using physiological internal and external solutions. As expected from the voltage clamp results, co-application of QX-314 and capsaicin inhibited the excitability of small diameter neurons, completely blocking action potential generation (FIG. 2, 15 of 15 neurons).

Figure 3A:
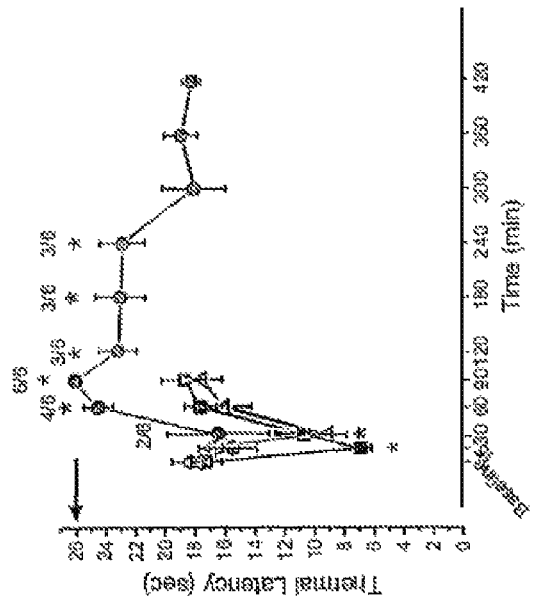
FIGS. 3A and 3B show that intraplantar injection of capsaicin (10 µg/10 µL) together with QX-314 (2%, 10 µL) leads to a prolonged local anesthesia to mechanical (von Frey filaments) and thermal noxious stimuli.

We next examined if the combination of capsaicin and QX-314 can reduce pain behavior in vivo. Injection of QX-314 alone (10 µL of 2% solution) into the hindpaw of adult rats had no significant effect on the mechanical threshold for eliciting a withdrawal response, as determined by von Frey hairs (p=0.33) (FIG. 3A). Capsaicin alone (10 µg/10 µL) elicited spontaneous flinching (40±6 flinches in 5 min), reflecting the direct irritant action of the capsaicin on nociceptors and after 15 and 30 minutes significantly reduced the mechanical threshold (p<0.05) (FIG. 3a), as expected. Injection of capsaicin and QX-314 together did not significantly change the number of flinches during the first 5 minutes after the injection (30±7, p=0.24). However, the combination completely abolished the later reduction in mechanical threshold normally produced by capsaicin alone (p=0.14, measured at 15 minutes). Moreover, 60 minutes after the combined injection of capsaicin and QX-314, mechanical threshold actually increased to reach twice the baseline value, two hours after injection (46±5 g vs. 24±3 g, p<0.05). In three animals the paw was insensitive to even the highest value von Frey filament (57 g). The elevated mechanical threshold lasted for about three hours and then gradually returned back to basal levels by four hours (FIG. 3A).

Figure 3B:
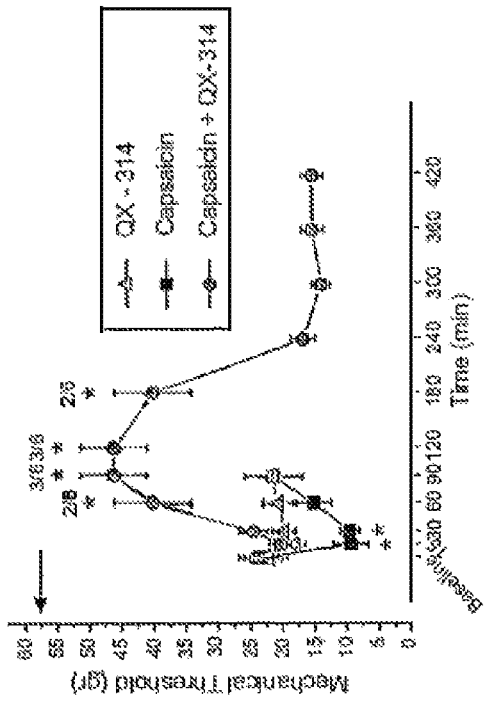

Similar effects were seen examining sensitivity to a standardized noxious radiant heat stimulus. Unexpectedly, QX-314 alone transiently reduced the thermal response latency at 30 min after the injection (p<0.01 at 30 min; p>0.05 for all other time points) (FIG. 3B). Capsaicin (10 µg/10 µL) alone also reduced as expected the thermal response latency (p<0.01 15 and 30 min) (FIG. 3B). However, while both QX-314 and capsaicin alone increased heat sensitivity, the co-application of QX-314 and capsaicin together progressively anesthetized the animals to noxious heat, such that 2 hours after the injection no animal reacted to the radiant noxious heat applied for 25 seconds. This effect remained for 4 hours after the injection (FIG. 3B).

Figure 4A:
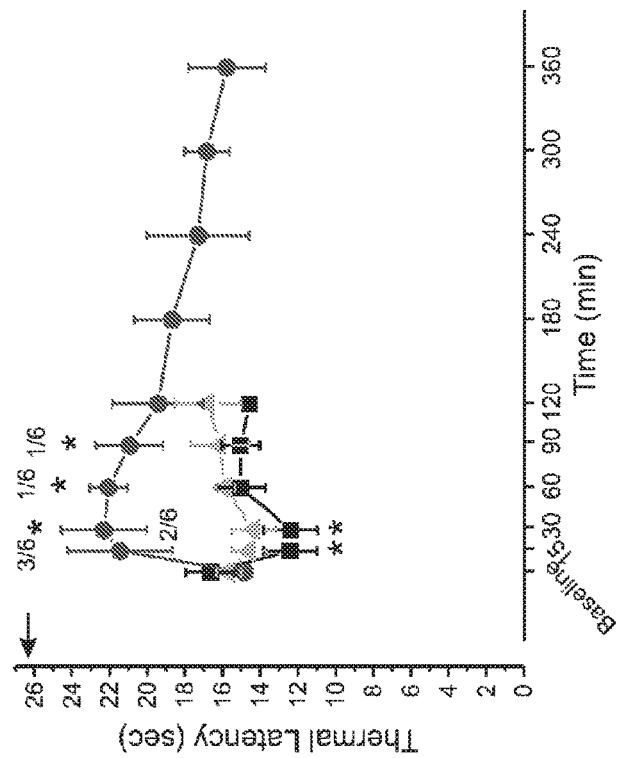
FIGS. 4A, 4B, and 4C show that injection of QX-314 followed by capsaicin adjacent to the sciatic nerve anesthetized the hindlimbs of the animals to noxious mechanical and thermal stimuli without producing any motor deficit.
Figure 4B:
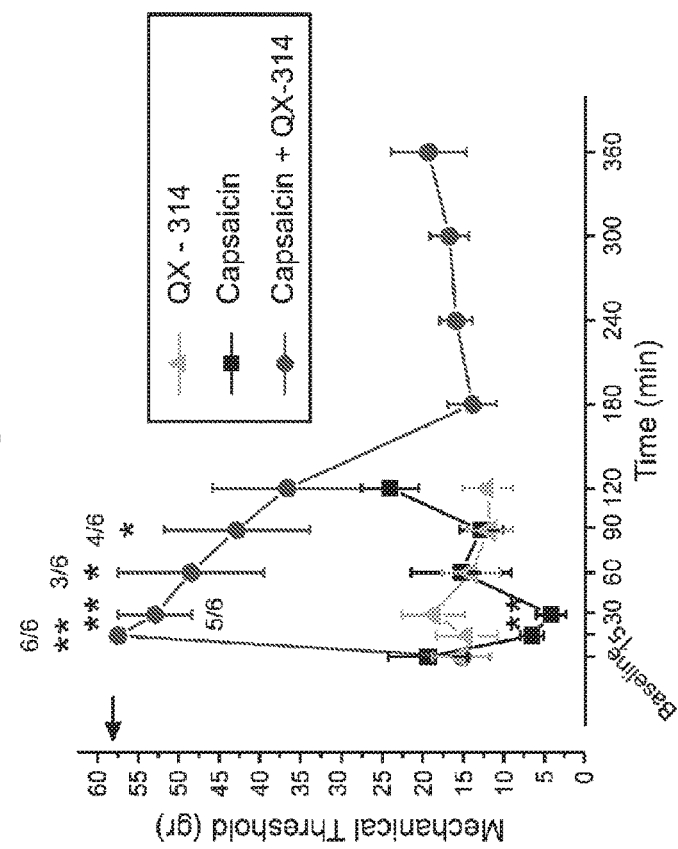
Figure 4C:
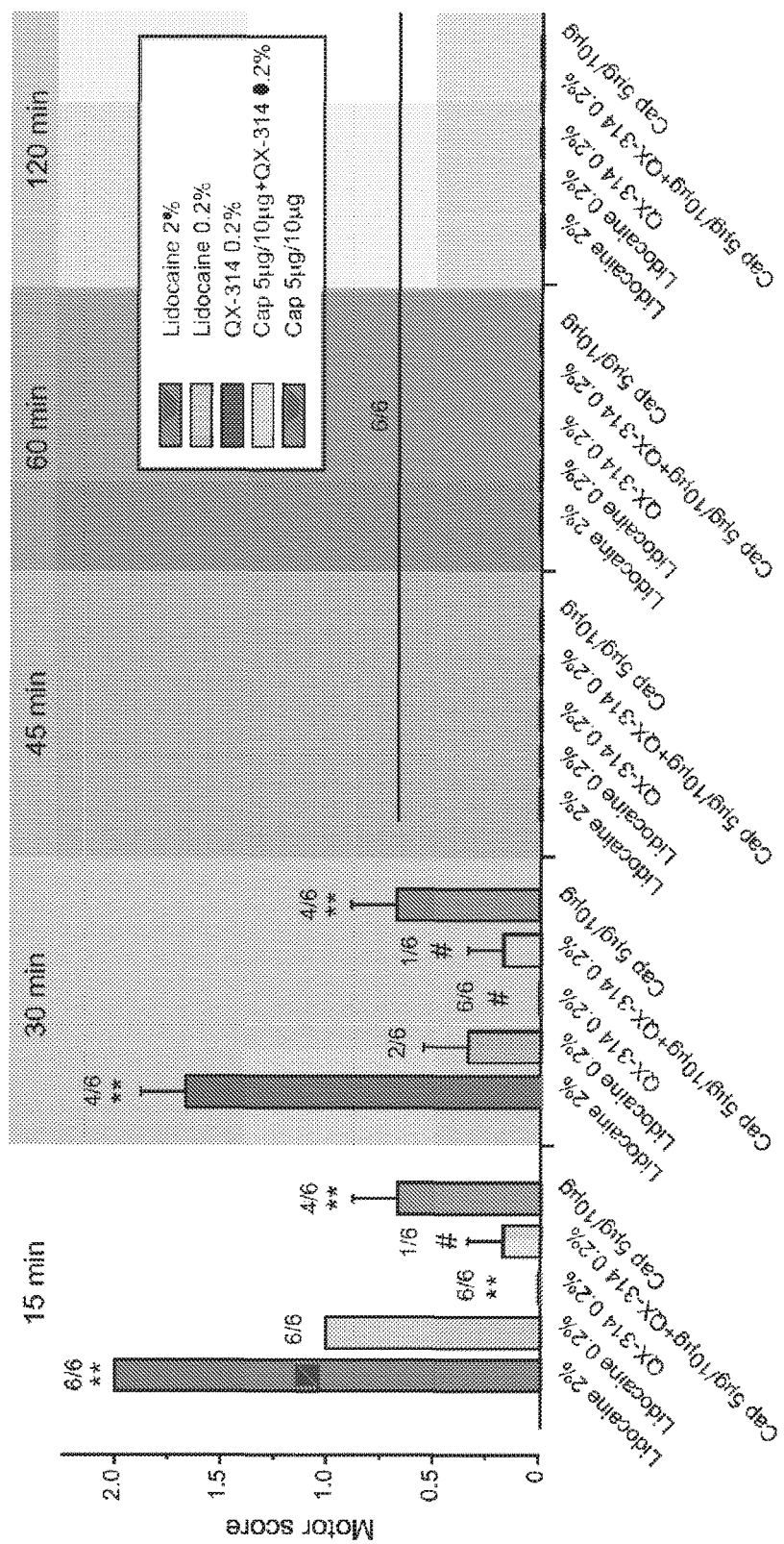

We next tested if capsaicin and QX-314 co-administration can be used to produce regional nerve block without the motor effects seen when local anesthesia is produced by lidocaine. Motor effects were scored according to a scale of 0 (no effect; normal gait and limb placement), 1 (limb movement but with abnormal limb placement and movement) or 2 (complete loss of limb movement). Injection of 2% lidocaine (a standard concentration for local nerve block) in close proximity to the sciatic nerve caused complete paralysis of the lower limb when assayed at 15 minutes (6 of 6 animals) and complete or partial paralysis was still present at 30 minutes (mean motor score 1.67±0.2, p<0.01; FIG. 4C). There was a complete loss of the tactile stimulus-evoked placing reflex lasting for at least 30 minutes in all animals with full recovery of these sensory and motor deficits by 45 minutes (FIG. 4). During the period of paralysis, it was not possible to assay sensory sensitivity. In pilot experiments with QX-314, it became clear that much lower concentrations of QX-314 than lidocaine could be used to produce effective local anesthesia when applied with capsaicin. Injection of QX-314 (0.2%, 100 µL) alone had no effect on motor function (6 of 6 animals; FIG. 4C) and also had no significant effect on either mechanical threshold (p=0.7) or thermal response latency (p=0.66) (FIG. 4A, 4B). Capsaicin alone (0.5 µg/µL, 100 µL) injected near the nerve reduced both mechanical threshold (p<0.05) and thermal latency (p<0.05) for 30 min after injection (FIG. 4A, 4B). During this period 4 out of the 6 animals demonstrated a sustained flexion of the injected limb leading to a slight impairment of locomotion (mean motor score 0.7±0.2, p<0.01) but movement of the knee and hip as well as the placing reflex were unchanged. We interpret the sensitivity and motor changes as reflecting activation of nociceptor axons producing a sustained flexion reflex. For co-application of QX-314 and capsaicin into the para-sciatic nerve region, we injected QX-314 first, followed 10 minutes later by capsaicin, with the idea that QX-314 would be present extracellularly and ready to enter TRPV1 channels as soon as they were activated. Indeed, there was little or no behavioral response to the capsaicin injection when preceded by QX-314 injection, and the behavioral responses indicated that there was effective anesthesia to noxious stimuli. There was a very marked increase in mechanical threshold such that all animals showed no response to the stiffest von Frey hair (57 g; vs. pre-injection withdrawal to stimuli averaging 15.2±3.4; p<0.01, n=6) and also in the thermal response latency (22.3±2.3 s vs. 14.9±0.4 s, p<0.05, n=6). These changes were evident at 15 min after the capsaicin injection for the mechanical stimuli and at 30 min for the thermal stimuli and lasted for 90 minutes (FIG. 4A, 4B). Five of six animals had no motor deficit whatsoever (mean motor score 0.17±0.17, p=0.34) (FIG. 4C) and no change in the placing reflex. One animal demonstrated sustained flexion similar to that observed when capsaicin was injected alone, but more transient.

Methods

Electrophysiology

Dorsal root ganglia from 6-8 week old Sprague-Dawley rats were removed and placed into Dulbecco's Minimum Essential Medium containing 1% penicillin—streptomycin (Sigma), then treated for 90 minutes with 5 mg/ml collagenase, 1 mg/ml Dispase II (Roche, Indianapolis, Ind.) and for 7 minutes with 0.25% trypsin, followed by addition of 2.5% trypsin inhibitor. Cells were triturated in the presence of DNAase I inhibitor (50 U), centrifuged through 15% BSA (Sigma), resuspended in 1 ml Neurobasal medium (Sigma), 10 µM AraC, NGF (50 ng/ml) and GDNF (2 ng/ml) and plated onto poly-lysine (500 µg/ml) and laminin (5 mg/ml) coated 35 mm tissue culture dishes (Becton Dickinson) at 8000-9000 per well. Cultures were incubated at 37° C., 5% carbon dioxide. Recordings were made within 48 hours after plating. Average size of small neurons chosen as likely nociceptors was 23±6 µm (n=50) and that of large neurons was 48±8 µm (n=10).

Whole-cell voltage-clamp or current-clamp recordings were made using an Axopatch 200A amplifier (Axon Instruments, Union City, Calif.) and patch pipettes with resistances of 1-2 MΩ. For voltage-clamp recordings pipette capacitance was reduced by wrapping the shank by Parafilm or coating the shank with Sylgard (Dow Corning, Midland, Mich.). Cell capacitance was compensated for using the amplifier circuitry, and linear leakage currents subtracted using a P/4 procedure. Series resistance (usually 3-7 MΩ and always less than 10 MΩ) was compensated by ~80%. Voltage clamp recordings used solutions designed to isolate sodium currents by blocking potassium and calcium currents and with reduced external sodium to improve voltage clamp. Pipette solution was 110 mM CsCl, 1 mM $CaCl_2$, 2 mM $MgCl_2$, 11 mM EGTA, and 10 mM HEPES, pH adjusted to 7.4 with ~25 mM CsOH. External solution was 60 mM NaCl, 60 mM choline chloride, 4 mM KCl, 2 mM $CaCl_2$, 1 mM $MgCl_2$, 0.1 mM $CdCl_2$, 15 mM tetraethylammonium chloride, 5 mM 4-aminopyridine, 10 mM glucose, and 10 mM HEPES, pH adjusted to 7.4 with NaOH. No correction was made for the small liquid junction potential (−2.2 mV).

Current clamp recordings were made using the fast current clamp mode of the Axopatch 200A amplifier Pipette solution was 135 mM K gluconate; 2 mM $MgCl_2$; 6 mM KCl; 10 mM HEPES; 5 mM Mg ATP; 0.5 mM $Li_2GTP$; (pH=7.4 with KOH). External solution was 145 mM NaCl; 5 mM KCl; 1 mM $MgCl_2$; 2 mM $CaCl_2$ 10 mM HEPES; 10 mM glucose; (pH adjusted to 7.4 with NaOH). Membrane potential was corrected for a liquid junction potential of −15 mV.

Command protocols were generated and data digitized using a Digidata 1200 A/D interface with pCLAMP 8.2 software (Axon Instruments, Union City, Calif.). Voltage-clamp current records were low pass filtered at 2 kHz and current clamp recordings at 10 kHz (−3 dB, 4 pole Bessel filter).

QX-314 (5 mM), capsaicin (1 µM or 500 nM), or their combination was applied using custom-designed multibarrel fast drug delivery system placed about 200-250 µm from the neuron. Solution exchange was complete in less than a second.

Behavior

For intraplantar injections, rats were first habituated to handling and tests performed with the experimenter blind to the treatment. Intraplantar injections of vehicle (20% ethanol, 5% Tween 20 in saline, 10 µL) capsaicin (1 µg/µL), QX-314 (2%) or mixture of capsaicin and QX-314 into the left hindpaw were made and mechanical and thermal sensitivities determined using von Frey hairs and radiant heat respectively.

For sciatic nerve injections, animals were first habituated to handling for 10 days. Lidocaine (0.2% or 2%, 100 µL); QX-314 (0.2%, 100 µL) alone; capsaicin (50 µg in 100 µL) alone, or QX-314 followed by capsaicin (10 minutes interval) were injected into the area of sciatic nerve below the hip joint. Mechanical and thermal thresholds were determined using von Frey filaments and radiant heat. Motor function of the injected leg was assessed every 15 minutes using the following grading score: 0=none; 1=partially blocked; and 2=fully blocked. Walking, climbing, walking on the rod and placing reflex were examined. Motor blockade was graded as none when gait was normal and there was no visible limb weakness; as partially blocked when the limb could move but movements were abnormal and could not support the normal posture; and as completely blocked when the limb was flaccid and without resistance to extension of the limb. All experiments were done with the experimenter blinded.

Statistical Analysis

Statistics were analyzed using Students t test or one-way ANOVA, followed by Dunnett's test as appropriate. For the motor scoring the data obtained after injection of lidocaine 0.2% used as a control for the Dunnett's test. Data represented as mean±SEM.

Example 2

Figure 5:
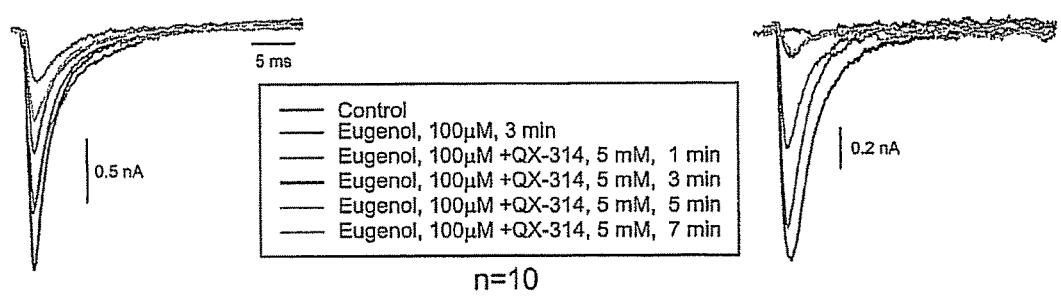
FIG. 5 shows voltage clamp recordings of sodium channel current in small dorsal root ganglion neurons. The data show that eugenol alone has a modest inhibitory effect on sodium current (10-20% inhibition). Co-application of eugenol and QX-314 produces progressive block that can be complete after 7 minutes. Two examples are depicted, which are representative of 10 experiments with similar results.

We have also shown that eugenol ($C_{10}H_{12}O_2$), an allyl chain-substituted guaiacol, 2-methoxy-4-(2-propenyl)phenol (active ingredient in oil of clove, and a non-pungent agonist of TRPV1 receptors) promotes entry of QX-314 into dorsal root ganglion neurons by activating TRPV1 channels. FIG. 5 depicts voltage clamp recordings of sodium channel current in small dorsal root ganglion neurons. The data show that eugenol alone has a modest inhibitory effect on sodium current (10-20% inhibition). Co-application of eugenol and QX-314 produces progressive block that can be complete after 7 minutes. Two examples are depicted, which are representative of 10 experiments with similar results. As is demonstrated above, external QX-314 alone has no effect while internal QX-314 blocks sodium channels. Thus, these experiments indicate that eugenol promotes entry of QX-314 into dorsal root ganglion neurons by activating TRPV1 channels.

Example 3

Figure 6:
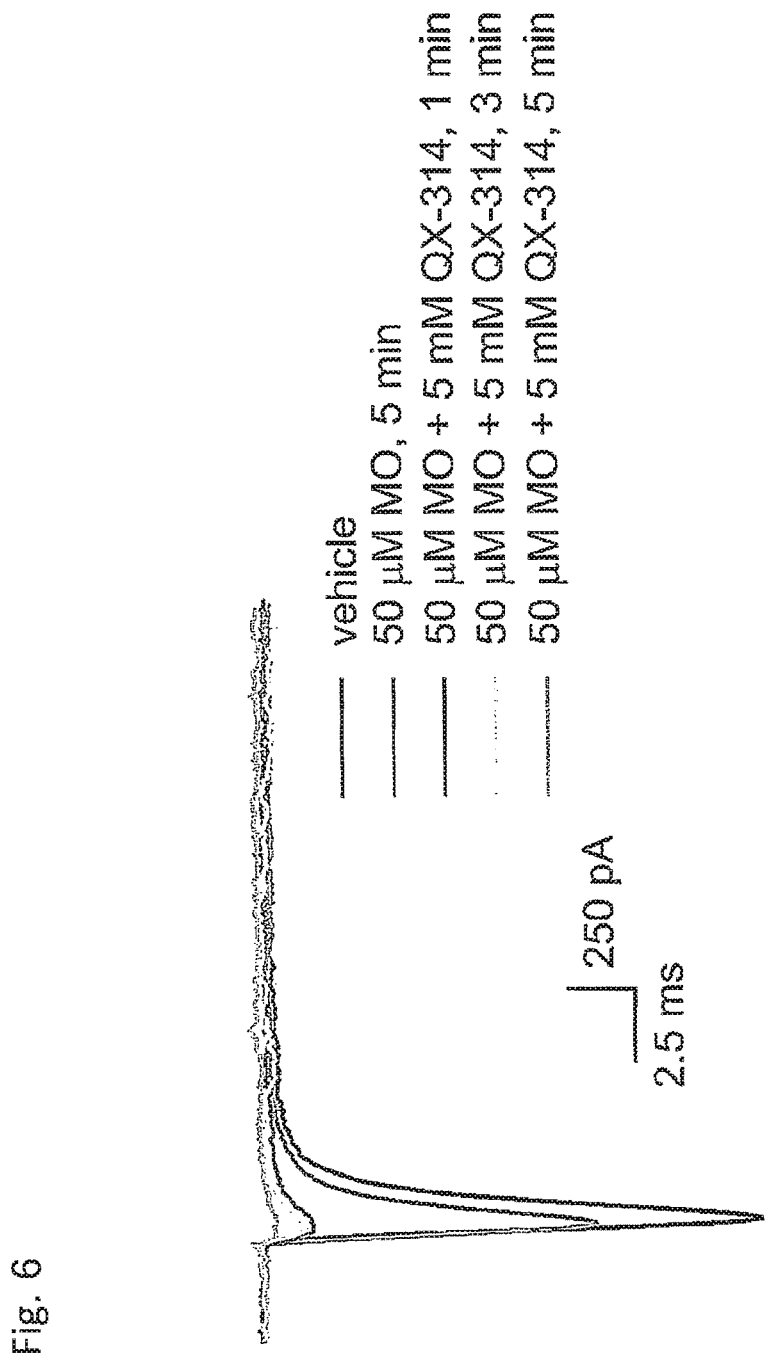
FIG. 6 shows the effects of co-application of the TRPA agonist mustard oil (MO) (50 µM) and QX-314 (5 mM). MO alone reduces sodium current by 20-30% and reaches a plateau after approximately 3 minutes. Co-application of MO and QX-314 reduced sodium current dramatically.

FIG. 6 shows the results of co-application of the TRPA agonist mustard oil (MO) (50 µM) and QX-314 (5 mM). MO alone reduces sodium current by 20-30% and reaches a plateau after approximately 3 minutes. Co-application of MO and QX-314 reduced sodium current dramatically.

Other Embodiments

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

The invention claimed is:

1. A method of treating itch in a human patient, said method comprising administering to said patient a compound represented by formula (I)

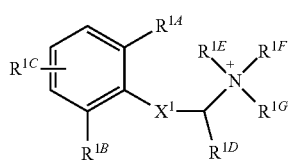

wherein each of $R^{1A}$, $R^{1B}$, and $R^{1C}$ is, independently, selected from H, halogen, $C_{1-4}$ alkyl, $C_{2-4}$ alkenyl, and $C_{2-4}$ alkynyl;

$X^1$ is selected from $-CR^{1W}R^{1X}-$, $-NR^{1Y}C(O)-$, $-OC(O)-$, $-SC(O)-$, $-C(O)NR^{1Z}-$, $-CO_2-$, and $-OC(S)-$;

each of $R^{1W}$, $R^{1X}$, $R^{1Y}$, and $R^{1Z}$ is, independently, selected from H, $C_{1-4}$ alkyl, $C_{2-4}$ alkenyl, $C_{2-4}$ alkynyl, and $C_{2-4}$ heteroalkyl;

$R^{1D}$ is selected from H, $C_{1-4}$ alkyl, $C_{2-4}$ alkenyl, $C_{2-4}$ alkynyl, and $C_{2-4}$ heteroalkyl; and each of $R^{1E}$, $R^{1F}$, and $R^{1G}$ is, independently, selected from $C_{1-4}$ alkyl, $C_{2-4}$ alkenyl, $C_{2-4}$ alkynyl, and $C_{2-4}$ heteroalkyl, or $R^{1D}$ and $R^{1G}$ together complete a heterocyclic ring having at least one nitrogen atom.

2. The method of claim 1, wherein said compound is selected from the group consisting of N-methyl etidocaine, N-methyl lidocaine, N,N-dimethyl prilocaine, N,N,N-trimethyl tocainide, N-methyl ropivacaine, N-methyl bupivacaine, N-methyl levobupivacaine, N-methyl mepivacaine, QX-314, N-methyl procaine, and QX-222.

3. The method of claim 1, wherein said compound is N-methyl etidocaine.

4. The method of claim 1, said method comprising topically administering said compound to said patient.

5. The method of claim 1, wherein said compound is formulated as a composition selected from the group consisting of a gel, ointment, paste, and cream.

6. The method of claim 5, wherein said compound is present in said composition in an amount of from 0.0001% to 25% (w/w).

7. The method of claim 5, wherein said compound is present in said composition in an amount of from 0.0001% to 10% (w/w).

8. The method of claim 5, wherein said compound is present in said composition in an amount of from 0.0005% to 4% (w/w).

* * * * *

UNITED STATES PATENT AND TRADEMARK OFFICE
CERTIFICATE OF CORRECTION

| | |
|---|---|
| PATENT NO. | : 10,179,116 B2 |
| APPLICATION NO. | : 15/470324 |
| DATED | : January 15, 2019 |
| INVENTOR(S) | : Bruce P. Bean et al. |

It is certified that error appears in the above-identified patent and that said Letters Patent is hereby corrected as shown below:

In the Specification

At Column 1, Lines 19-20, please insert the following section:
-- GOVERNMENT SUPPORT
This invention was made with government support under NS039518 awarded by the National Institutes of Health. The government has certain rights in the invention. --

Signed and Sealed this
Twenty-seventh Day of August, 2024

Katherine Kelly Vidal
*Director of the United States Patent and Trademark Office*